(12) United States Patent
Qin et al.

(10) Patent No.: US 10,385,056 B2
(45) Date of Patent: Aug. 20, 2019

(54) 4-SUBSTITUTED PYRROLO[2,3-D]PYRIMIDINE COMPOUND AND USE THEREOF

(71) Applicant: JIANGSU CAREFREE PHARMACEUTICAL CO., LTD, Nanjing (CN)

(72) Inventors: Yinlin Qin, Nanjing (CN); Mei Su, Nanjing (CN); Shousheng Yan, Nanjing (CN); Xianzhi Wu, Nanjing (CN); Tao Chen, Nanjing (CN); Jianhua Jiang, Nanjing (CN)

(73) Assignee: JIANGSU CAREFREE PHARMACEUTICAL CO., LTD, Nanjing, JS (CN)

( * ) Notice: Subject to any disclaimer, the term of this patent is extended or adjusted under 35 U.S.C. 154(b) by 0 days.

(21) Appl. No.: 15/112,196

(22) PCT Filed: Mar. 24, 2015

(86) PCT No.: PCT/CN2015/074989
§ 371 (c)(1),
(2) Date: Jul. 18, 2016

(87) PCT Pub. No.: WO2015/110092
PCT Pub. Date: Jul. 30, 2015

(65) Prior Publication Data
US 2016/0333015 A1 Nov. 17, 2016

(30) Foreign Application Priority Data

Jan. 24, 2014 (CN) .......................... 2014 1 0036561

(51) Int. Cl.
*A61K 31/519* (2006.01)
*C07D 487/04* (2006.01)
*A61K 31/55* (2006.01)

(52) U.S. Cl.
CPC .......... *C07D 487/04* (2013.01); *A61K 31/519* (2013.01); *A61K 31/55* (2013.01)

(58) Field of Classification Search
CPC ........................... A61K 31/519; C07D 487/04
USPC ........................................ 514/265.1; 544/280
See application file for complete search history.

*Primary Examiner* — Jeffrey H Murray
(74) *Attorney, Agent, or Firm* — George G. Wang; Bei & Ocean

(57) ABSTRACT

The invention relates to a 4-substituted pyrrolo[2,3-d]pyrimidine compound and the use thereof in preparing medications for treating JAK-targeted diseases such as rheumatoid, immune system diseases, and tumor. The 4-substituted pyrrolo[2,3-d]pyrimidine compound of the invention is as shown in chemical formula I.

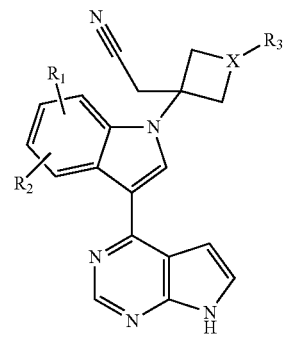

The activity experimental results of the invention show that the new compound has obvious effect and activity in inhibition of Janus kinases, JAK-STAT, cell proliferation of human lymphocytoma, and rheumatoid arthritis.

7 Claims, No Drawings

4-SUBSTITUTED PYRROLO[2,3-D]PYRIMIDINE COMPOUND AND USE THEREOF

TECHNICAL FIELD

The invention relates to a 4-substituted pyrrolo[2,3-d]pyrimidine compound and the use thereof in preparing medications for treating JAK-targeted diseases such as immune system diseases, rheumatoid and tumor.

BACKGROUND OF THE INVENTION

Protein kinase, also known as protein phosphakinase, is a kind of enzyme for catalyzing protein phosphorylation reaction. Such enzyme can transfer γ-phosphoric acid on ATP to the amino acid residue of protein molecule so as to change the conformations and activities of protein and enzyme. Phosphorylation of protein is an important step in transduction of multiple signals, and most of important life activities in the cell depend upon the phosphorylation of protein. The enzyme is a key factor for regulating cell signals including cell proliferation and cell differentiation.

The protein kinase signal has two important roles in transduction: one is to regulate the activity of protein by phosphorylation, phosphorylation/dephosphorylation is the common mechanism for reversible activation of most signal path components, some proteins are active after phosphorylation and some are active after dephosphorylation; the other is to gradually amplify signal and cause cell reaction by gradual phosphorylation of proteins.

Janus-activated kinase\signal transducer and activator of transcription (JAK-STAT) is a recently discovered signal transduction path in cells closely related to cytokines, involving in many important biological processes such as cell proliferation, differentiation, apoptosis and immunoregulation. Janus-activated kinase is a non-receptor tyrosine protein kinase which has 4 family members including JAK1, JAK2, TYK2 and JAK3/. JAK is a kind of very important drug targets. It has been proven that JAK inhibitor can be used for preparing medications for treating blood system diseases, tumor, rheumatoid arthritis, psoriasis, etc. at present. Since JAK inhibitor has obvious medical use and can be used for preparing medications for treating various diseases, it is extremely useful for studying and finding such compound.

China patent application No. CN 102026999A discloses an azetidine and cyclobutane derivative and the combination, use and preparation method thereof. They can be JAK inhibitors used for treating JAK-related diseases such as inflammatory diseases, autoimmune diseases and cancer. The parent nucleus structure is shown as the following chemical formula. As an effective JAK inhibitor, it can be taken as a bulk drug for preparing medications for treating diseases such as rheumatoid arthritis, dermatosis, cancer and myeloproliferative disease.

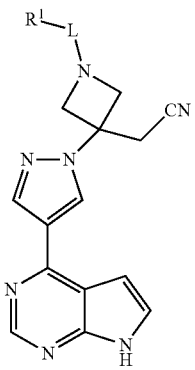

Currently, Tofacitinib of Pfizer has been listed as a typical JAK inhibitor and it is the pioneered drug for treating rheumatoid arthritis. Nevertheless, the treatment field of JAK inhibitor involves different aspects, and the direction of research is to find more new compounds with strong activity and high druggability.

SUMMARY OF THE INVENTION

The first technical purpose of the invention is to provide a new JAK inhibitor compound; the second technical purpose of the invention is to provide an application of the said JAK inhibitor compound in preparing medications for treating diseases related to JAK inhibitor.

In order to realize the technical purposes of the invention, the technical scheme of the invention is as follows:

I. A compound as shown in chemical formula I,

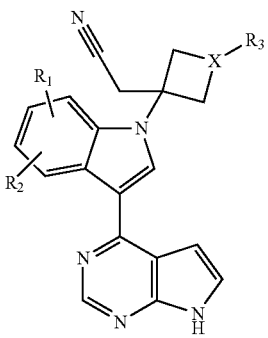

where, R1 and R2 are substituents at any position of benzene ring and independently selected from: hydrogen linked to an aromatic ring, any halogen atom, —(CH$_Z$)nCN, —(CH$_Z$)nCH$_3$,

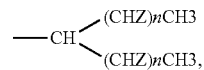

n=0-3, Z=0-2; or -Cyn, or —(CH$_Z$)nCYn, or —(CH$_Z$)n, or —O(CH$_Z$)n CH3, or cycloalkanes of C3-C6.

The —(CH$_Z$)nCN group is a general expression of cyano-substituent, where, n=0-3, Z=1-2, i.e., the corresponding structure comprises cyano, ethyl cyano, propyl cyano and corresponding alkene or alkynyl cyano.

The —(CH$_Z$)nCH$_3$ or —(CH$_Z$)n group is a general expression of alkyl substituent, where, n=0-3, Z=1-2, i.e., the corresponding structure comprises alkane, olefin and alkyne groups having 1-4 carbons.

The

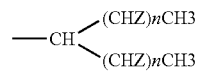

group (n=0-3, Z=0-2) corresponds to branched paraffin groups such as isopropyl, isobutyl and isopentyl.

For the —(CH$_Z$)nCYn group, n=0-3, Z=1-2, and Y is any halogen atom, i.e., the corresponding structure comprises alkane, olefin and alkyne groups having 1-4 carbons with terminal arbitrarily substituted by 0-3 halogen atoms (one of F, Cl, Br and I).

For the -nY group, n=0-3, and Y is any halogen atom, i.e., the corresponding structure comprises a group with 0-3 halogen atoms (one of F, Cl, Br and I) arbitrarily substituted on the aromatic benzene ring.

For the -Cyn group, n=0-3, and Y is any halogen atom, i.e., the corresponding structure comprises methyl group with 0-3 halogen atoms (one of F, Cl, Br and I) arbitrarily substituted on the aromatic benzene ring.

The —O(CH$_Z$)nCH3 group is a general expression of alcoxyl substituent, where, n=0-3, Z=0-2, i.e., the corresponding structure comprises alkane, olefin and alkyne oxo groups having 1-4 carbons.

R3 is:

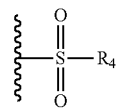

wherein, R4 is selected from hydrogen, alkyl of (C1-C4), alkenyl of (C2-C4), alkynyl of (C2-C4) and cycloalkanes of C3-C7, or

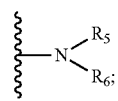

R5 and R6 are selected from hydrogen, alkyl of (C1-C4), alkenyl of (C2-C4), alkynyl of (C2-C4) or cycloalkanes of C3-C7; R5 and R6 are the same or different;

Or, R3 is

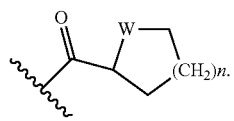

W is S, N or C, n is 1-3; and
X is CH$_2$ or N.

The above structural formula shows that R3 of the structural formula I of the invention mainly involves in two types of groups, one type is sulfonic acid group with alkyl substituent and the other type is carbonyl group with heterocyclic alkyl substituent; said alkyl group comprises alkane, cycloalkane, olefin and alkyne groups; and said heterocyclic alkyl group comprises N heterocyclic alkane, O heterocyclic alkane and S heterocyclic alkane.

II. The preparation method of compound as shown in the said chemical formula of the invention comprises the following steps:

(1) Adding amino protecting group to the secondary amine of said compound in compound A structure to obtain compound B.

For example, preferably, the amino protecting agent used in a certain example of the invention is triisopropylchlorosilane (TIPSCl).

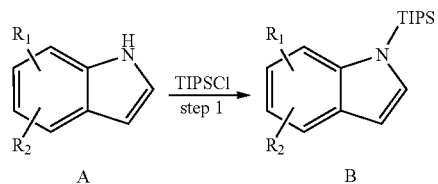

(2) Substituting hydrogen of compound B at the position as shown in the following chemical reaction formula by bromine to form compound C.

Wherein, in a certain example of the invention, the reaction substrate used by the said bromo-substitution method is N-bromo-succinimide (NBS).

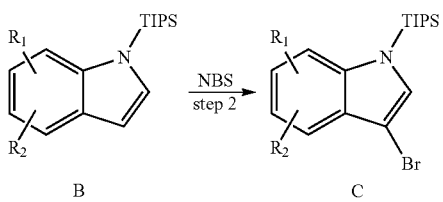

(3) Making compound C react with bispinacolatodiboronmin (Pin$_2$B$_2$) to form compound D.

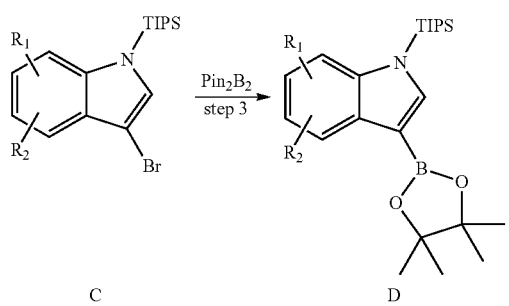

(4) Making compound D react with compound E to form compound F under alkaline environment.

The said alkaline environment comprises solid inorganic base and organic base. Preferably, inorganic bases such as sodium carbonate, sodium bicarbonate, sodium hydroxide, or organic bases such as triethylamine and N,N-diisopropylethylamine are selected as acid-binding agents in the example of the invention.

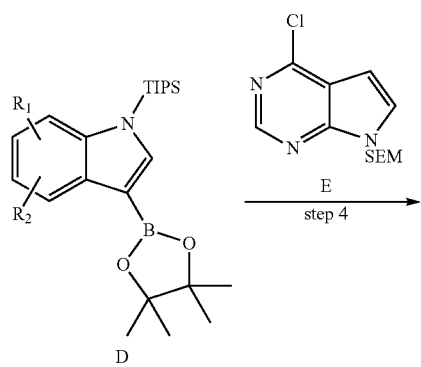
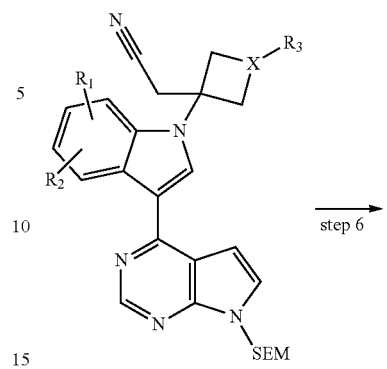

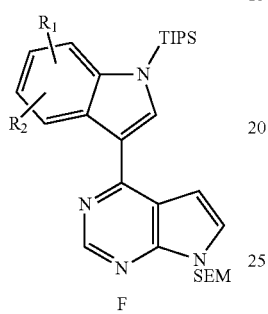

(5) Making compound F react with compound G, and taking 1,8-diazabicyclo[5.4.0]undec-7-ene (DBU) as catalyst to form compound H.

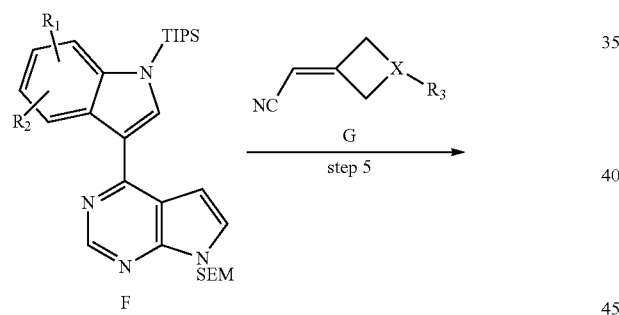

(6) Removing protecting group 2-(trimethylsilyl) ethoxymethyl from compound H in presence of strong acid or strong alkaline to obtain the target product I protected in the patent. For example, preferably, the strong acid or strong alkaline used in one example of the invention is trifluoroacetic acid.

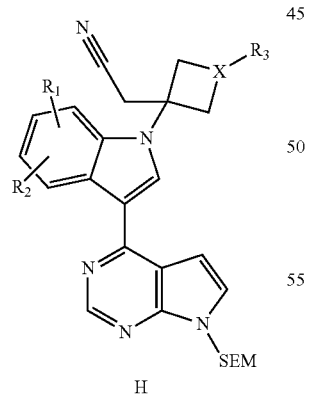

To sum up, the general chemical reaction equation of the said preparation method is as follows:

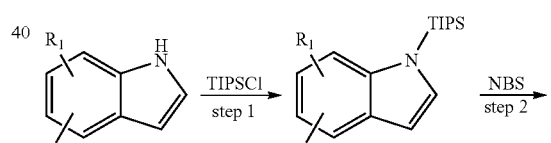

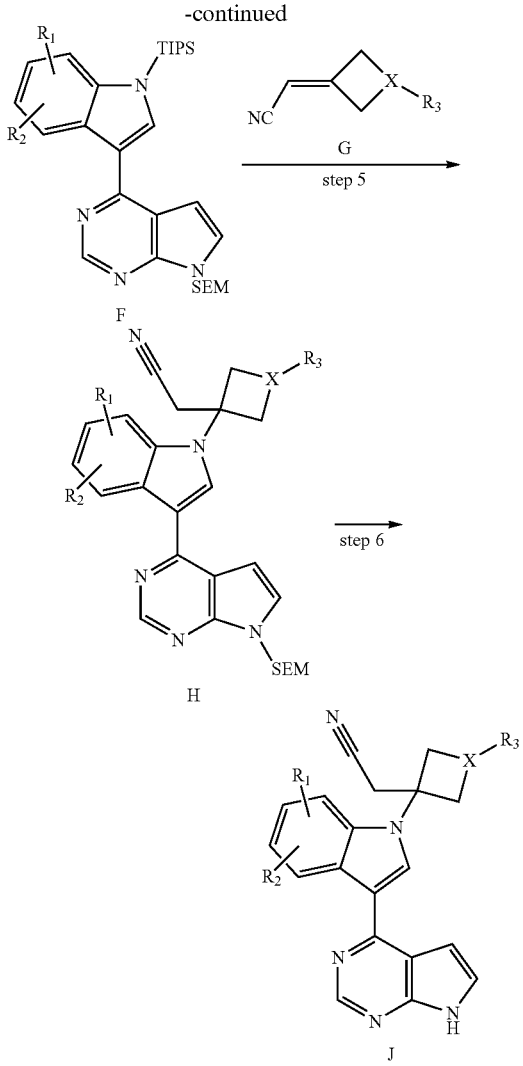

Wherein, the indicated structures of $R_2$, $R_2$, $R_3$ and X included in the structural formula are in conformity with those specified in the first technical scheme.

III. Further, the invention also protects a pharmaceutically acceptable salt of the said compound as shown in chemical formula I.

A person skilled in the art understands that the pharmaceutically acceptable salt of the said compound of the invention is the salt for producing non-toxic compound with the compound of the invention, for example, sodium salt, sylvite and metal ion salts often used in pharmacy. In addition, a person skilled in the art understands that the technical effect of the above addition salt is to further promote the bioavailability of medications in human body, and the pharmaceutical activity and focus treatment effect of the salt are the same as those of the raw material compound.

IV. Further, the invention also protects an optical isomer of the said compound as shown in chemical formula I.

A person skilled in the art understands that the optical isomer of the said compound as shown in chemical formula I can predictably have the same technical effect as the compound of the invention, i.e., the pharmaceutical activity and focus treatment effect of the optical isomer are the same as those of the raw material compound.

V. In addition, the invention also protects a pharmaceutically acceptable acid addition salt of the said compound as shown in chemical formula.

A person skilled in the art understands that acid for the pharmaceutically acceptable acid addition salt of the said compound of the invention is the acid of non-toxic compound produced by the compound of the invention and also the pharmaceutically acceptable addition salt produced by the said alkali of the invention, for example, hydrochloride, hydrobromide, hydriodate, trifluoride formate, sulfate, disulfate, nitrate, phosphate, hydrophosphate, acetate, propionic acid, crylic acid, malonic acid, butyric acid, oxalate, lactate, citrate, acid citrate, tartrate, bitartrate, succinate, maleate, fumarate, maleate, cinnamate, vanillate, malate, gluconate, mesylate, esilate, benzene sulfonate, benzoate, tosilate, etc. In addition, a person skilled in the art understands that the technical effect of the above addition salt is to further promote the bioavailability of medications in human body, and the pharmaceutical activity and focus treatment effect of the addition salt are the same as those of the raw material compound.

For the description of the preferred embodiments, the said compound as shown in the said chemical formula I of the invention includes but not limited to the following compounds, as shown in Table 1:

TABLE 1

| Example No. | Chemical formula | Chemical name | Preparation method |
|---|---|---|---|
| 1 | | 2-(3-(3-(7H-pyrrole[2,3-d]pyrimidine-4-yl)-1H-indole-1-yl)-1-(ethyl sulfonyl) azetidine-3-yl)acetonitrile | Example 1 |

TABLE 1-continued

| Example No. | Chemical formula | Chemical name | Preparation method |
|---|---|---|---|
| 2 | | 2-(3-(3-(7H-pyrrole[2,3-d]pyrimidine-4-yl)-1H-indole-1-yl)-1-(methyl sulfonyl)azetidine-3-yl)acetonitrile | Same as Example 1 |
| 3 | | 2-(3-(3-(7H-pyrrole[2,3-d]pyrimidine-4-yl)-1H-indole-1-yl)-1-(propyl sulfonyl)azetidine-3-yl)acetonitrile | Same as Example 1 |
| 4 | | 2-(3-(3-(7H-pyrrole[2,3-d]pyrimidine-4-yl)-1H-indole-1-yl)-1-(isopropyl sulfonyl)azetidine-3-yl)acetonitrile | Same as Example 1 |

TABLE 1-continued

| Example No. | Chemical formula | Chemical name | Preparation method |
|---|---|---|---|
| 5 | 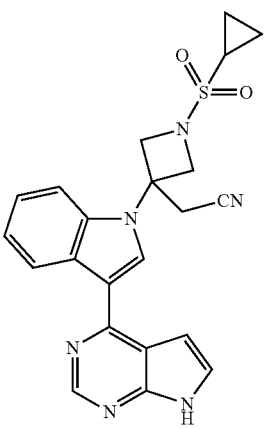 [SMILES: N#CCC1(n2cc(-c3ncnc4[nH]ccc34)c3ccccc32)CN(S(=O)(=O)C2CC2)C1] | 2-(3-(3-(7H-pyrrole[2,3-d]pyrimidine-4-yl)-1H-indole-1-yl)-1-(cyclopropyl sulfonyl)azetidine-3-yl)acetonitrile | Same as Example 1 |
| 6 | 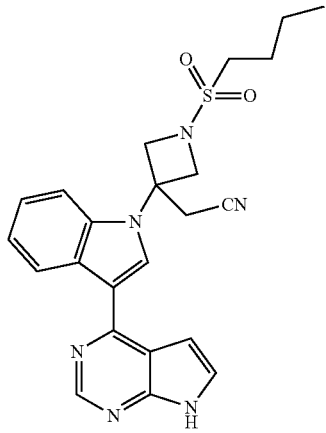 [SMILES: CCCCS(=O)(=O)N1CC(CC#N)(n2cc(-c3ncnc4[nH]ccc34)c3ccccc32)C1] | 2-(3-(3-(7H-pyrrole[2,3-d]pyrimidine-4-yl)-1H-indole-1-yl)-1-(butyl sulfonyl) azetidine-3-yl)acetonitrile | Same as Example 1 |
| 7 | 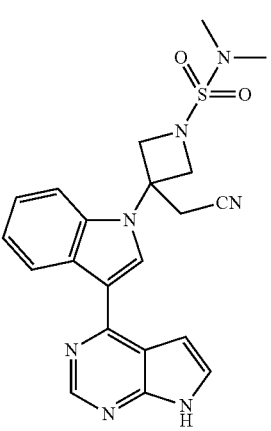 [SMILES: CN(C)S(=O)(=O)N1CC(CC#N)(n2cc(-c3ncnc4[nH]ccc34)c3ccccc32)C1] | 2-(3-(3-(7H-pyrrole[2,3-d]pyrimidine-4-yl)-1H-indole-1-yl)-3-(ethyl cyano)-N,N-dimethyl azetidine-1-sulfanilamide | Example 7 |

TABLE 1-continued

| Example No. | Chemical formula | Chemical name | Preparation method |
|---|---|---|---|
| 8 | | 2-(3-(3-(7H-pyrrole[2,3-d]pyrimidine-4-yl)-1H-indole-1-yl)-3-(ethyl cyano)-N,N-methyl ethyl azetidine-1-sulfanilamide | Example 7 |
| 9 | | 2-(3-(3-(7H-pyrrole[2,3-d]pyrimidine-4-yl)-1H-indole-1-yl)-3-(ethyl cyano)-N,N-diethyl azetidine-1-sulfanilamide | Same as Example 7 |
| 10 | | 2-(3-(3-(7H-pyrrole[2,3-d]pyrimidine-4-yl)-1H-indole-1-yl)-3-(ethyl cyano)-pyrrolidine-1-sulfanilamide | Same as Example 7 |

TABLE 1-continued

| Example No. | Chemical formula | Chemical name | Preparation method |
|---|---|---|---|
| 11 | | 2-(3-(3-(7H-pyrrole[2,3-d]pyrimidine-4-yl)-1H-indole-1-yl)-1-(pyrrolidine-2-carbonyl)azetidine-3-yl)acetonitrile | Example 11 |
| 12 | | 2-(3-(3-(7H-pyrrole[2,3-d]pyrimidine-4-yl)-1H-indole-1-yl)-1-(piperidine-2-carbonyl)azetidine-3-yl)acetonitrile | Same as Example 11 |
| 13 | | 2-(3-(3-(7H-pyrrole[2,3-d]pyrimidine-4-yl)-1H-indole-1-yl)-1-(azacycloheptane-2-carbonyl)azetidine-3-yl)acetonitrile | Example 11 |
| 14 | | 2-(3-(3-(7H-pyrrole[2,3-d]pyrimidine-4-yl)-1H-indole-1-yl)-1-(tetrahydrofuran-2-carbonyl)azetidine-3-yl)acetonitrile | Same as Example 11 |

TABLE 1-continued

| Example No. | Chemical formula | Chemical name | Preparation method |
| --- | --- | --- | --- |
| 15 | | 2-(3-(3-(7H-pyrrole[2,3-d]pyrimidine-4-yl)-1H-indole-1-yl)-1-(tetrahydropyridine-2-carbonyl)azetidine-3-yl)acetonitrile | Same as Example 11 |
| 16 | | 2-(3-(3-(7H-pyrrolo[2,3-d]pyrimidine-4-yl)-1H-indole-1-yl)-1-(oxacycloheptane-2-carbonyl)azetidine-3-yl)acetonitrile | Same as Example 11 |
| 17 | | 2-(3-(3-(7H-pyrrole[2,3-d]pyrimidine-4-yl)-1H-indole-1-yl)-1-(tetrahydrothiophene-2-carbonyl)azetidine-3-yl)acetonitrile | Same as Example 11 |
| 18 | | 2-(3-(3-(7H-pyrrole[2,3-d]pyrimidine-4-yl)-1H-indole-1-yl)-1-(tetrahydrothiapyran-2-carbonyl)azetidine-3-yl)acetonitrile | Same as Example 11 |

TABLE 1-continued

| Example No. | Chemical formula | Chemical name | Preparation method |
|---|---|---|---|
| 19 | | 2-(3-(3-(7H-pyrrole[2,3-d]pyrimidine-4-yl)-1H-indole-1-yl)-1-(thiacycloheptane-2-carbonyl)azetidine-3-yl)acetonitrile | Same as Example 11 |
| 20 | | 2-(1-(ethyl sulfonyl)-3-(6-fluoro-3-(7H-pyrrole[2,3-d]pyrimidine-4-yl)-1H-indole-1-yl)azetidine-3-yl)acetonitrile | Example 20 |
| 21 | | 2-(1-(methyl sulfonyl)-3-(6-fluoro-3-(7H-pyrrole[2,3-d]pyrimidine-4-yl)-1H-indole-1-yl)azetidine-3-yl)acetonitrile | Same as Example 20 |

TABLE 1-continued

| Example No. | Chemical formula | Chemical name | Preparation method |
|---|---|---|---|
| 22 | | 2-(1-(propyl sulfonyl)-3-(6-fluoro-3-(7H-pyrrole[2,3-d]pyrimidine-4-yl)-1H-indole-1-yl)azetidine-3-yl)acetonitrile | Same as Example 20 |
| 23 | | 2-(1-(isopropyl sulfonyl)-3-(6-fluoro-3-(7H-pyrrole[2,3-d]pyrimidine-4-yl)-1H-indole-1-yl)azetidine-3-yl)acetonitrile | Example 20 |
| 24 | | 2-(1-(cyclopropyl sulfonyl)-3-(6-fluoro-3-(7H-pyrrole[2,3-d]pyrimidine-4-yl)-1H-indole-1-yl)azetidine-3-yl)acetonitrile | Same as Example 20 |

TABLE 1-continued

| Example No. | Chemical formula | Chemical name | Preparation method |
|---|---|---|---|
| 25 | | 2-(1-(methyl sulfonyl)-3-(6-chloro-3-(7H-pyrrole[2,3-d]pyrimidine-4-yl)-1H-indole-1-yl)azetidine-3-yl)acetonitrile | Same as Example 20 |
| 26 | | 2-(1-(ethyl sulfonyl)-3-(6-chloro-3-(7H-pyrrole[2,3-d]pyrimidine-4-yl)-1H-indole-1-yl)azetidine-3-yl)acetonitrile | Same as Example 20 |
| 27 | | 2-(1-(propyl sulfonyl)-3-(6-chloro-3-(7H-pyrrole[2,3-d]pyrimidine-4-yl)-1H-indole-1-yl)azetidine-3-yl)acetonitrile | Same as Example 20 |

TABLE 1-continued

| Example No. | Chemical formula | Chemical name | Preparation method |
|---|---|---|---|
| 28 | | 2-(1-(isopropyl sulfonyl)-3-(6-chloro-3-(7H-pyrrole[2,3-d]pyrimidine-4-yl)-1H-indole-1-yl)azetidine-3-yl)acetonitrile | Same as Example 20 |
| 29 | | 2-(1-(cyclopropyl sulfonyl)-3-(6-chloro-3-(7H-pyrrole[2,3-d]pyrimidine-4-yl)-1H-indole-1-yl)azetidine-3-yl)acetonitrile | Same as Example 20 |
| 30 | | 2-(1-(methyl sulfonyl)-3-(6-bromo-3-(7H-pyrrole[2,3-d]pyrimidine-4-yl)-1H-indole-1-yl)azetidine-3-yl)acetonitrile | Same as Example 20 |

TABLE 1-continued

| Example No. | Chemical formula | Chemical name | Preparation method |
|---|---|---|---|
| 31 | | 2-(1-(ethyl sulfonyl)-3-(6-bromo-3-(7H-pyrrole[2,3-d]pyrimidine-4-yl)-1H-indole-1-yl)azetidine-3-yl)acetonitrile | Same as Example 20 |
| 32 | | 2-(1-(methyl sulfonyl)-3-(5,6-difluoro-3-(7H-pyrrole[2,3-d]pyrimidine-4-yl)-1H-indole-1-yl)azetidine-3-yl)acetonitrile | Same as Example 20 |
| 33 | | 2-(1-(ethyl sulfonyl)-3-(5,6-difluoro-3-7H-pyrrole[2,3-d]pyrimidine-4-yl)-1H-indole-1-yl)azetidine-3-yl)acetonitrile | Same as Example 20 |

TABLE 1-continued

| Example No. | Chemical formula | Chemical name | Preparation method |
|---|---|---|---|
| 34 | | 2-(1-(propyl sulfonyl)-3-(5,6-difluoro-3-(7H-pyrrole[2,3-d]pyrimidine-4-yl)-1H-indole-1-yl)azetidine-3-yl)acetonitrile | Same as Example 20 |
| 35 | | 2-(1-(cyclopropyl sulfonyl)-3-(5,6-difluoro-3-(7H-pyrrole[2,3-d]pyrimidine-4-yl)-1H-indole-1-yl)azetidine-3-yl)acetonitrile | Same as Example 20 |
| 36 | | 2-(1-(methyl sulfonyl)-3-(6,7-difluoro-3-(7H-pyrrole[2,3-d]pyrimidine-4-yl)-1H-indole-1-yl)azetidine-3-yl)acetonitrile | Same as Example 20 |

TABLE 1-continued

| Example No. | Chemical formula | Chemical name | Preparation method |
|---|---|---|---|
| 37 | | 2-(1-(ethyl sulfonyl)-3-(6,7-difluoro-3-(7H-pyrrole[2,3-d]pyrimidine-4-yl)-1H-indole-1-yl)azetidine-3-yl)acetonitrile | Same as Example 20 |
| 38 | | 2-(1-(propyl sulfonyl)-3-(6,7-difluoro-3-(7H-pyrrole[2,3-d]pyrimidine-4-yl)-1H-indole-1-yl)azetidine-3-yl)acetonitrile | Same as Example 20 |
| 39 | | 2-(1-(isopropyl sulfonyl)-3-(6,7-difluoro-3-(7H-pyrrole[2,3-d]pyrimidine-4-yl)-1H-indole-1-yl)azetidine-3-yl)acetonitrile | Same as Example 20 |

TABLE 1-continued

| Example No. | Chemical formula | Chemical name | Preparation method |
|---|---|---|---|
| 40 | | 2-(1-(cyclopropyl sulfonyl)-3-(6,7-difluoro-3-(7H-pyrrole[2,3-d]pyrimidine-4-yl)-1H-indole-1-yl)azetidine-3-yl)acetonitrile | Same as Example 20 |
| 41 | | 2-(1-(methyl sulfonyl)-3-(6,8-difluoro-3-(7H-pyrrole[2,3-d]pyrimidine-4-yl)-1H-indole-1-yl)azetidine-3-yl)acetonitrile | Same as Example 20 |
| 42 | | 2-(1-(ethyl sulfonyl)-3-(6,8-difluoro-3-(7H-pyrrole[2,3-d]pyrimidine-4-yl)-1H-indole-1-yl)azetidine-3-yl)acetonitrile | Same as Example 20 |

TABLE 1-continued

| Example No. | Chemical formula | Chemical name | Preparation method |
|---|---|---|---|
| 43 | | 2-(1-(propyl sulfonyl)-3-(6,8-difluoro-3-(7H-pyrrole[2,3-d]pyrimidine-4-yl)-1H-indole-1-yl)azetidine-3-yl)acetonitrile | Same as Example 20 |
| 44 | | 2-(1-(isopropyl sulfonyl)-3-(6,8-difluoro-3-(7H-pyrrole[2,3-d]pyrimidine-4-yl)-1H-indole-1-yl)azetidine-3-yl)acetonitrile | Same as Example 20 |
| 45 | | 2-(1-(cyclopropyl sulfonyl)-3-(6,8-difluoro-3-(7H-pyrrole[2,3-d]pyrimidine-4-yl)-1H-indole-1-yl)azetidine-3-yl)acetonitrile | Same as Example 20 |

TABLE 1-continued

| Example No. | Chemical formula | Chemical name | Preparation method |
|---|---|---|---|
| 46 | | 2-(1-(ethyl sulfonyl)-3-(5,7-difluoro-3-(7H-pyrrole[2,3-d]pyrimidine-4-yl)-1H-indole-1-yl)azetidine-3-yl)acetonitrile | Same as Example 20 |
| 47 | | 2-(1-(ethyl sulfonyl)-3-(5,7-difluoro-3-(7H-pyrrole[2,3-d]pyrimidine-4-yl)-1H-indole-1-yl)azetidine-3-yl)acetonitrile | Same as Example 20 |
| 48 | | 2-(1-(ethyl sulfonyl)-3-(5,8-difluoro-3-(7H-pyrrole[2,3-d]pyrimidine-4-yl)-1H-indole-1-yl)azetidine-3-yl)acetonitrile | Same as Example 20 |

TABLE 1-continued

| Example No. | Chemical formula | Chemical name | Preparation method |
|---|---|---|---|
| 49 | 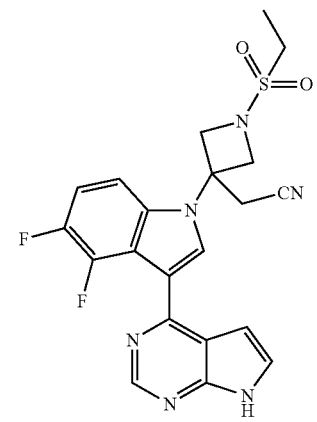 [SMILES: CCS(=O)(=O)N1CC(CC#N)(n2cc(-c3ncnc4[nH]ccc34)c3c(F)c(F)ccc32)C1] | 2-(1-(ethyl sulfonyl)-3-(7,8-difluoro-3-(7H-pyrrole[2,3-d]pyrimidine-4-yl)-1H-indole-1-yl)azetidine-3-yl)acetonitrile | Same as Example 20 |
| 50 | 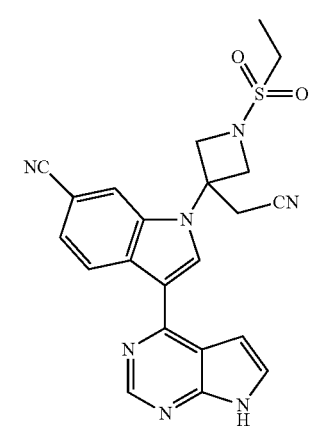 [SMILES: CCS(=O)(=O)N1CC(CC#N)(n2cc(-c3ncnc4[nH]ccc34)c3ccc(C#N)cc32)C1] | 2-(1-(ethyl sulfonyl)-3-(6-cyano-3-(7H-pyrrole[2,3-d]pyrimidine-4-yl)-1H-indole-1-yl)azetidine-3-yl)acetonitrile | Same as Example 20 |
| 51 | 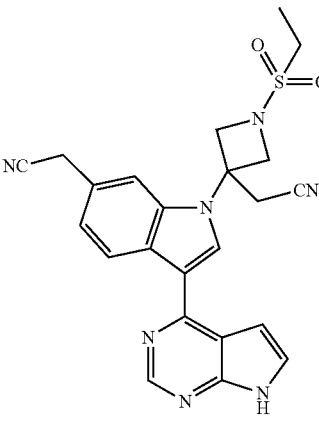 | 2-(1-(ethyl sulfonyl)-3-(6-ethyl cyano-3-(7H-pyrrole[2,3-d]pyrimidine-4-yl)-1H-indole-1-yl)azetidine-3-yl)acetonitrile | Same as Example 20 |

TABLE 1-continued

| Example No. | Chemical formula | Chemical name | Preparation method |
|---|---|---|---|
| 52 | | 2-(1-(ethyl sulfonyl)-3-(6-trifluoromethyl-3-(7H-pyrrole[2,3-d]pyrimidine-4-yl)-1H-indole-1-yl)azetidine-3-yl)acetonitrile | Same as Example 20 |
| 53 | | 2-(1-(ethyl sulfonyl)-3-(6-trifluoroethyl-3-(7H-pyrrole[2,3-d]pyrimidine-4-yl)-1H-indole-1-yl)azetidine-3-yl)acetonitrile | Same as Example 20 |
| 54 | | 2-(1-(ethyl sulfonyl)-3-(6-methyl-3-(7H-pyrrole[2,3-d]pyrimidine-4-yl)-1H-indole-1-yl)azetidine-3-yl)acetonitrile | Same as Example 20 |

TABLE 1-continued

| Example No. | Chemical formula | Chemical name | Preparation method |
|---|---|---|---|
| 55 | | 2-(1-(ethyl sulfonyl)-3-(6-ethyl-3-(7H-pyrrole[2,3-d]pyrimidine-4-yl)-1H-indole-1-yl)azetidine-3-yl)acetonitrile | Same as Example 20 |
| 56 | | 2-(1-(ethyl sulfonyl)-3-(6-propyl-3-(7H-pyrrole[2,3-d]pyrimidine-4-yl)-1H-indole-1-yl)azetidine-3-yl)acetonitrile | Same as Example 20 |
| 57 | | 2-(1-(ethyl sulfonyl)-3-(6-isopropyl-3-(7H-pyrrole[2,3-d]pyrimidine-4-yl)-1H-indole-1-yl)azetidine-3-yl)acetonitrile | Same as Example 20 |

TABLE 1-continued

| Example No. | Chemical formula | Chemical name | Preparation method |
|---|---|---|---|
| 58 | | 2-(1-(ethyl sulfonyl)-3-(6-methoxyl-3-(7H-pyrrole[2,3-d]pyrimidine-4-yl)-1H-indole-1-yl)azetidine-3-yl)acetonitrile | Same as Example 20 |
| 59 | | 2-(1-(ethyl sulfonyl)-3-(6-ethyoxyl-3-(7H-pyrrole[2,3-d]pyrimidine-4-yl)-1H-indole-1-yl)azetidine-3-yl)acetonitrile | Same as Example 20 |
| 60 | | 2-(1-(ethyl sulfonyl)-3-(6-propoxyl-3-(7H-pyrrole[2,3-d]pyrimidine-4-yl)-1H-indole-1-yl)azetidine-3-yl)acetonitrile | Same as Example 20 |

TABLE 1-continued

| Example No. | Chemical formula | Chemical name | Preparation method |
|---|---|---|---|
| 61 | | 2-(1-(ethyl sulfonyl)-3-(6-isopropoxyl-3-(7H-pyrrole[2,3-d]pyrimidine-4-yl)-1H-indole-1-yl)azetidine-3-yl)acetonitrile | Same as Example 20 |
| 62 | | 2-(1-(ethyl sulfonyl)-3-(5-fluoro-3-(7H-pyrrole[2,3-d]pyrimidine-4-yl)-1H-indole-1-yl)azetidine-3-yl)acetonitrile | Same as Example 20 |
| 63 | | 2-(1-(ethyl sulfonyl)-3-(5-trifluoromethyl-3-(7H-pyrrole[2,3-d]pyrimidine-4-yl)-1H-indole-1-yl)azetidine-3-yl)acetonitrile | Same as Example 20 |
| 64 | | 2-(1-(ethyl sulfonyl)-3-(5-methoxyl-3-(7H-pyrrole[2,3-d]pyrimidine-4-yl)-1H-indole-1-yl)azetidine-3-yl)acetonitrile | Same as Example 20 |

III. Application of the said compound as shown in chemical formula I of the invention in preparing medications for treating diseases related to JAK-activated kinase.

Further, the said application specifically comprises application for preparing medications for treating autoimmune diseases; application for preparing medications for treating rheumatoid arthritis; or application for preparing anti-tumor drugs.

The activity testing examples of Examples 67-69 of the invention show that the new compound in the form of the structural formula I of the invention has obvious function and activity on inhibition of Janus-activated kinase and in-vivo model of related diseases.

DETAILED DESCRIPTION OF THE PREFERRED EMBODIMENT

The following examples are used for describing the invention in details. The embodiments are provided for describing the technical purposes and beneficial effects of the invention, but not for limiting the invention in any way. A person skilled in the art uses records of claims, description and summary of the invention to easily realize that the basically identical technical scheme results can be obtained by changing or modifying various non-critical parameters and these results will fall into the protection scope of claims of the invention.

Example 1

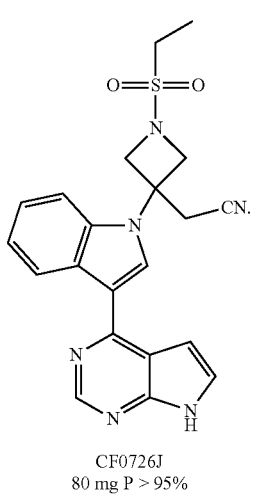 [SMILES: CCS(=O)(=O)N1CC(CC#N)(n2cc(-c3ncnc4[nH]ccc34)c3ccccc32)C1]

CF0726J
80 mg P > 95%

Preparation Method:
1) Step 1: Synthesis of CF0726A

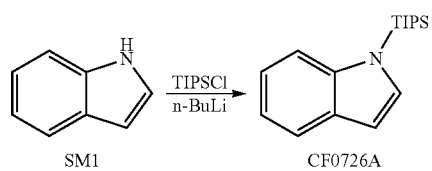

Dissolving raw material SM1 (24 g, 0.205 mol) in THF (240 mL), cooling to about −78° C. under the protection of nitrogen, slowly dropwise adding n-BuLi (106 mL, 0.265 mol, 1.3 eq), and keeping and stirring for 1 h after addition. Slowly dropwise adding TIPSCl (52.8 g, 0.274 mol, 1.3 eq), keeping temperature at about −78° C., and then keeping and reacting for 1 h after addition, performing TLC tracking reaction, adding water for quenching after the reaction, using EA for extraction, spinning it dry to obtain 73 g of yellow oily crude product, and directly carrying out the next reaction without purification.

2) Step 2: Synthesis of CF0726B

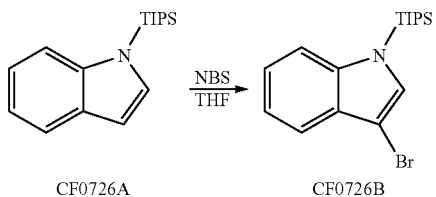

Dissolving CF0726A (36.5 g, P=90%, 0.121 mol) in THF (365 mL), cooling to about −78° C., slowly adding NBS (23 g, 0.129 mol, 1.07 eq), keeping for 1 h after addition and performing LCMS tracking reaction. Adding water for quenching after the reaction, using EA for extraction, spinning it dry to obtain 50 g of faint yellow oily crude product and making alkaline Al$_2$O$_3$ pass the column to obtain 21.4 g of white solid product (PE eluted).

3) Step 3: Synthesis of CF0726C

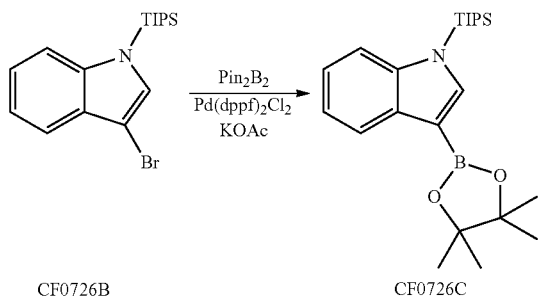

Placing CF0726B (12.5 g, P91.7%, 0.0327 mol), Pin2B2 (41.5 g, 0.163 mol, 5 eq), KOAc (16 g, 0.163 mol, 5 eq), Pd(dppf) Cl2 (2 g, 0.0026 mol, 0.08 eq) in a 250 mL three-necked flask, vacuumizing with an oil pump for 30 min, adding dioxane (140 mL) and reacting overnight at 80-95° C. under the protection of nitrogen. Performing LCMS tracking, adding DCM for dilution after the reaction, filtering and removing insoluble substances, using H$_2$O/DCM for extraction, spinning the organic phase dry to obtain 10 g of faint yellow oily crude product (including approximate 30% of product, Pin2B2 and CF0726A).

4) Step 4: Synthesis of CF0726E

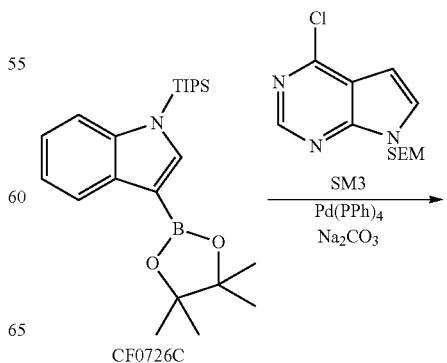

-continued

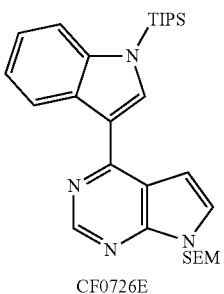
CF0726E

Dissolving raw material CF0726C (10 g, P30%, 0.0075 mol), SM3 (2.1 g, 0.0074 mol, 1 eq), Na2CO3 (1.59 g, 0.015 mol, 2 eq) and Pd(PPh$_3$)$_4$ (0.26 g, 0.000225 mol, 0.03 eq) in ethanol/water (80 mL, 1:1), performing the reaction at about 80° C., performing LCMS tracking, refilling SM3 until the raw material disappears, adding DCM for dilution after the reaction, filtering and removing insoluble substances, using H$_2$O/DCM for extraction, spinning the organic phase dry to obtain 8.5 g of yellow oily crude product, and directly performing the next reaction without purification (containing about 21.6% of product).

5) Step 5: Synthesis of CF0726F

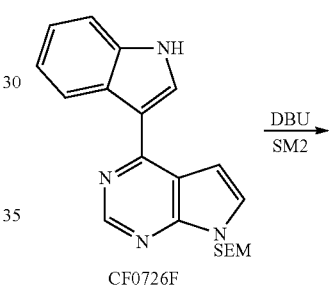

Dissolving raw material CF0726E (8.5 g, P21.6%, 0.0035 mol) and TBAF (4.3 g, 0.0165 mol, 4.7 eq) in THF (85 mL), performing room-temperature stirring and LCMS tracking, spinning it dry after the reaction, adding H$_2$O/EA for extraction, spinning the organic phase dry, making it pass the column to obtain white solid product (PE/EA=1:4 eluted) so as to obtain 1 g of white solid product.

6) Step 6: Synthesis of SM2

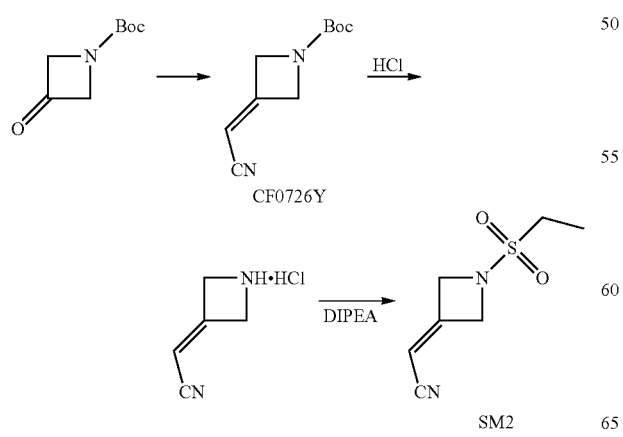

1, Dissolving cyanomethyl diethyl phosphate in THF (75 mL), cooling to −7−−5° C. under the protection of nitrogen, dropwise adding potassium tert-butoxide/THF (3.6 g is dissolved in 35 mL of THF), keeping for 3 h after addition, dropwise adding 1-Boc-3-azetidinone/THF solution (5 g is dissolved in 15 mL of THF), keeping for 1 h and then stirring overnight at room temperature, using EA/H2O for extraction after adding water for quenching, spinning it dry to obtain 8 g of crude product, and putting the product into the column to obtain 4.3 g of white solid product CF0726Y.

2, Dissolving raw material CF0726Y (0.4 g, 0.0021 mol) in dioxane solution (10 mL) of saturated hydrogen chloride, clearly dissolving it and separating white solid out, spinning solvent dry after raw material disappears, adding THF (10 mL) to dissolve it, then dropwise adding DIPEA (0.8 g, 6.18 mmol, 3 eq), stirring for 10 min, dropwise adding ethylsulfonyl chloride (0.32 g, 0.0025 mol, 1.2 eq), performing room-temperature stirring and LCMS tracking, spinning it dry after the reaction, using EA/H$_2$O for extraction, washing it once with NaHCO$_3$ and washing with saturated saline solution, spinning it dry to obtain 0.3 g of yellow oily crude product.

7) Step 7: Synthesis of CF0726H

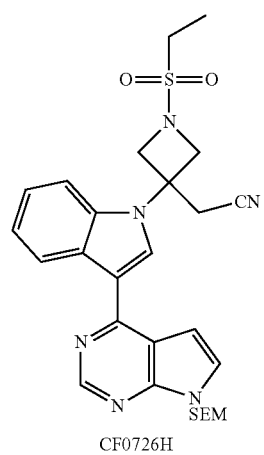
CF0726H

Dissolving raw material CF0726F (0.1 g, 0.00027 mol) in acetonitrile (5 mL), adding SM2 (0.1 g, 0.00054 mol, 2 eq) and DBU (0.1 g, 0.00066 mol, 2.4 eq), performing room-temperature stirring overnight, spinning it dry after the reaction, using H$_2$O/EA for extraction, spinning the organic phase dry and making it pass the column to obtain 0.19 g of product (PE/EA=3:1-1:1).

8) Step 8: Synthesis of CF0726J

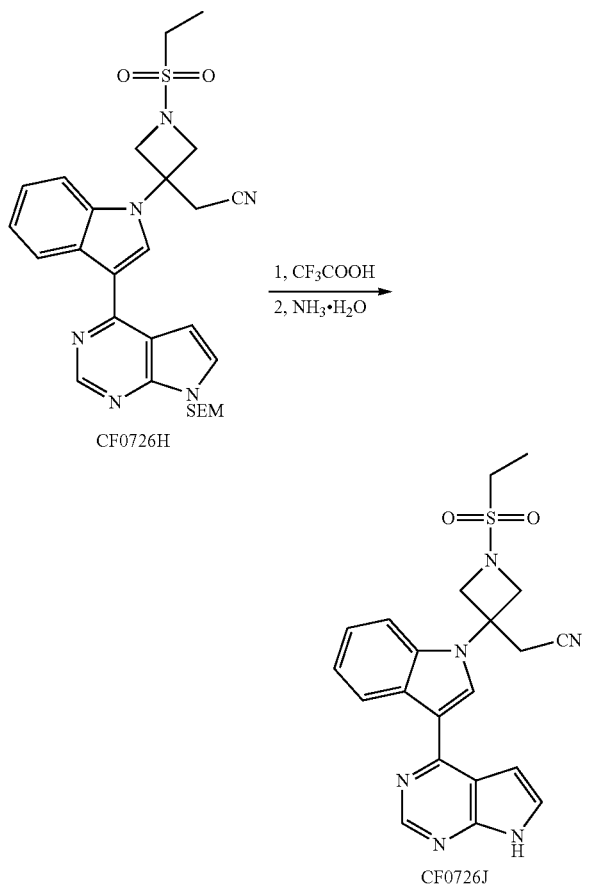

Dissolving raw material CF0726F (0.19 g, 0.00035 mol) into DCM (5 mL), adding TFA (2 mL), performing room-temperature stirring and LCMS tracking, spinning it dry after the reaction, adding DCM and re-spinning it dry twice to remove excess acid, adding methyl alcohol for dissolution, adding saturated ammonia (10 mL), performing room-temperature stirring and separating solid out, performing LCMS tracking, adding ice to cool it after the reaction, filtering and drying to obtain 80 mg of faint yellow product.
MS ES+: 421.2
1H-NMR (400 MHz, DMSO); δ (ppm): 7.09-8.80 (m, 8H, aromatic —H), 4.73 (d, 2H, J=42-CN), 3.22 (q, J=7.2 Hz, 2H, S—CH2-CH3), 1.24 (t, J=2.0 Hz, 3H, S—CH2-CH3)

The compound of Examples 2-6 can be prepared by the preparation method similar to Example 1:

Example 2

2-(3-(3-(7H-pyrrole[2,3-d]pyrimidine-4-yl)-1H-indole-1-yl)-1-(methyl sulfonyl)azetidine-3-yl)acetonitrile.

Example 3

2-(3-(3-(7H-pyrrole[2,3-d]pyrimidine-4-yl)-1H-indole-1-yl)-1-(propyl sulfonyl)azetidine-3-yl)acetonitrile.

Example 4

2-(3-(3-(7H-pyrrole[2,3-d]pyrimidine-4-yl)-1H-indole-1-yl)-1-(isopropyl sulfonyl)azetidine-3-yl)acetonitrile.

Example 5

2-(3-(3-(7H-pyrrole[2,3-d]pyrimidine-4-yl)-1H-indole-1-yl)-1-(cyclopropyl sulfonyl)azetidine-3-yl)acetonitrile.

Example 6

2-(3-(3-(7H-pyrrole[2,3-d]pyrimidine-4-yl)-1H-indole-1-yl)-1-(butyl sulfonyl)azetidine-3-yl)acetonitrile.

Example 7

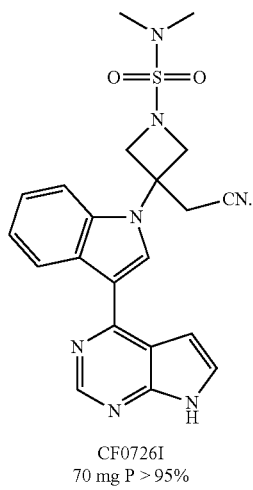 [SMILES: CN(C)S(=O)(=O)N1CC(CC#N)(n2cc(-c3ncnc4[nH]ccc34)c3ccccc32)C1]

CF0726I
70 mg P > 95%

Preparation Method:
1) Step 1: Synthesis of CF0726A

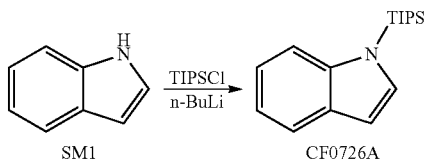

Dissolving raw material SM1 (24 g, 0.205 mol) in THF (240 mL), cooling to about −78° C. under the protection of nitrogen, slowly dropwise adding n-BuLi (106 mL, 0.265 mol, 1.3 eq), and keeping and stirring for 1 h after addition. Slowly dropwise adding TIPSCl (52.8 g, 0.274 mol, 1.3 eq), keeping temperature at about −78° C., and then keeping and reacting for 1 h after addition, performing TLC tracking reaction, adding water for quenching after the reaction, using EA for extraction, spinning it dry to obtain 73 g of yellow oily crude product, and directly carrying out the next reaction without purification.

2) Step 2: Synthesis of CF0726B

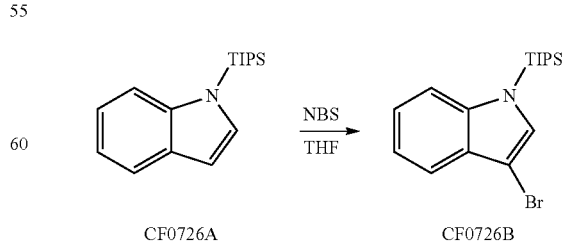

Dissolving CF0726A (36.5 g, P=90%, 0.121 mol) in THF (365 mL), cooling to about −78° C., slowly adding NBS (23 g, 0.129 mol, 1.07 eq), keeping for 1 h after addition and performing LCMS tracking reaction. Adding water for quenching after the reaction, using EA for extraction, spinning it dry to obtain 50 g of faint yellow oily crude product and making alkaline Al$_2$O$_3$ pass the column to obtain 21.4 g of white solid product (PE eluted).

3) Step 3: Synthesis of CF0726C

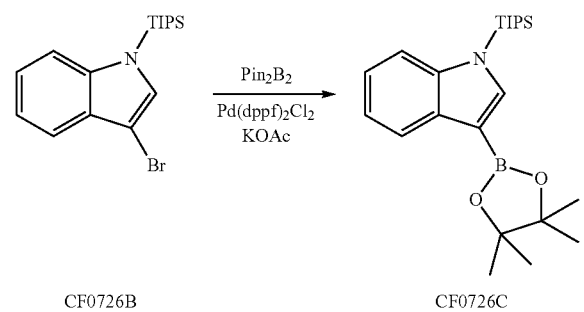

Placing CF0726B (12.5 g, P91.7%, 0.0327 mol), Pin2B2 (41.5 g, 0.163 mol, 5 eq), KOAc (16 g, 0.163 mol, 5 eq), Pd (dppf) Cl2 (2 g, 0.0026 mol, 0.08 eq) in a 250 mL three-necked flask, vacuumizing with an oil pump for 30 min, adding dioxane (140 mL) and reacting overnight at 80-95° C. under the protection of nitrogen. Performing LCMS tracking, adding DCM for dilution after the reaction, filtering and removing insoluble substances, using H$_2$O/DCM for extraction, and spinning the organic phase dry to obtain 10 g of faint yellow oily crude product (including approximate 30% of product, Pin2B2 and CF0726A).

4) Step 4: Synthesis of CF0726E

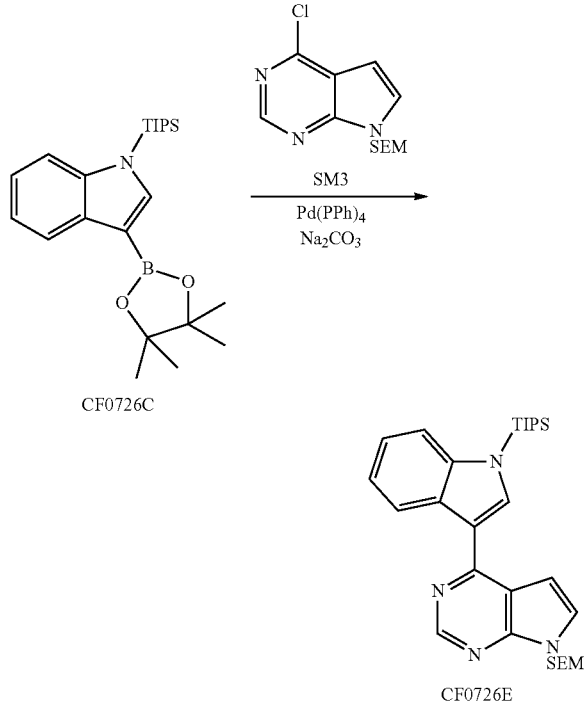

Dissolving raw material CF0726C (10 g, P30%, 0.0075 mol), SM3 (2.1 g, 0.0074 mol, 1 eq), Na2CO3 (1.59 g, 0.015 mol, 2 eq) and Pd(PPh$_3$)$_4$ (0.26 g, 0.000225 mol, 0.03 eq) in ethanol/water (80 mL, 1:1), performing the reaction at about 80° C., performing LCMS tracking, refilling SM3 until the raw material disappears, adding DCM for dilution after the reaction, filtering and removing insoluble substances, using H$_2$O/DCM for extraction, spinning the organic phase dry to obtain 8.5 g of yellow oily crude product, and directly performing the next reaction without purification (containing about 21.6% of product).

5) Step 5: Synthesis of CF0726F

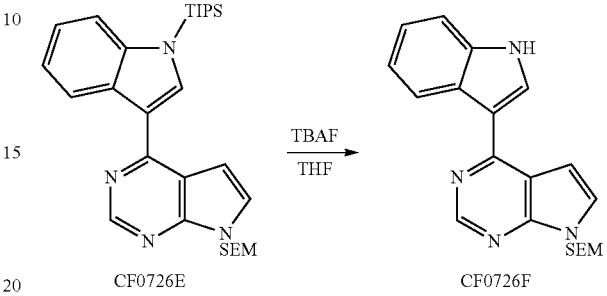

Dissolving raw material CF0726E (8.5 g, P21.6%, 0.0035 mol) and TBAF (4.3 g, 0.0165 mol, 4.7 eq) in THF (85 mL), performing room-temperature stirring and LCMS tracking, spinning it dry after the reaction, adding H$_2$O/EA for extraction, spinning the organic phase dry, making it pass the column to obtain white solid product (PE/EA=1:4 eluted) so as to obtain 1 g of white solid product.

6) Step 6: Synthesis of SM2

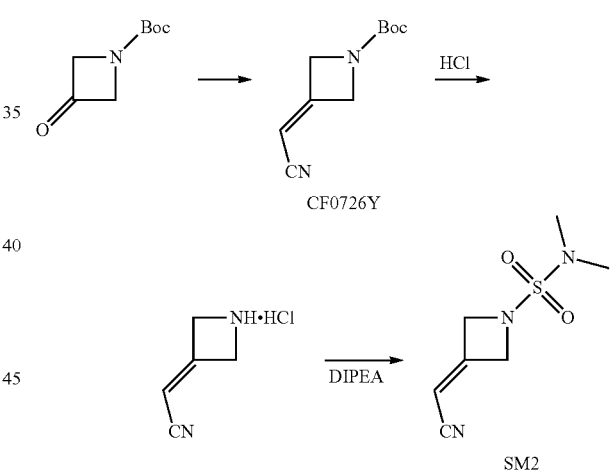

1, Dissolving cyanomethyl diethyl phosphate in THF (75 mL), cooling to −7--5° C. under the protection of nitrogen, dropwise adding potassium tert-butoxide/THF (3.6 g is dissolved in 35 mL of THF), keeping for 3 h after addition, dropwise adding 1-Boc-3-azetidinone/THF solution (5 g is dissolved in 15 mL of THF), keeping for 1 h and then stirring overnight at room temperature, using EA/H2O for extraction after adding water for quenching, spinning it dry to obtain 8 g of crude product, and putting the product into the column to obtain 4.3 g of white solid product CF0726Y.

2, Dissolving raw material CF0726Y (0.5 g, 0.0026 mol) in dioxane solution (10 mL) of saturated hydrogen chloride, clearly dissolving it and separating white solid out, spinning solvent dry after raw material disappears, adding THF (10 mL) to dissolve it, then dropwise adding DIPEA (1.0 g, 7.75 mmol, 3 eq), stirring for 10 min, dropwise adding N,N-dimethylsulfamoyl chloride (0.4 g, 0.0028 mol, 1.1 eq), performing room-temperature stirring and LCMS tracking, spinning it dry after the reaction, using EA/H₂O for extraction, washing it once with NaHCO₃ and washing with saturated saline solution, spinning it dry to obtain 0.55 g of yellow oily crude product.

7) Step 7: Synthesis of CF0726H

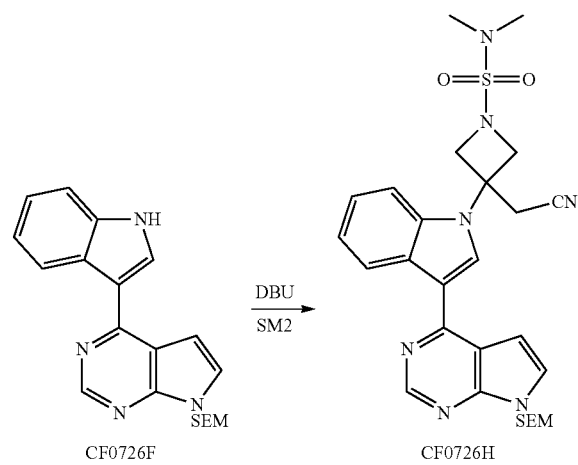

Dissolving raw material CF0726F (0.1 g, 0.00027 mol) in acetonitrile (5 mL), adding SM2 (0.1 g, 0.0005 mol, 1.8 eq) and DBU (0.1 g, 0.00066 mol, 2.4 eq), performing room-temperature stirring overnight, spinning it dry after the reaction, using H₂O/EA for extraction, spinning the organic phase dry and making it pass the column to obtain 0.1 g of product (PE/EA=3:1-1:1).

8) Step 8: Synthesis of CF0726I

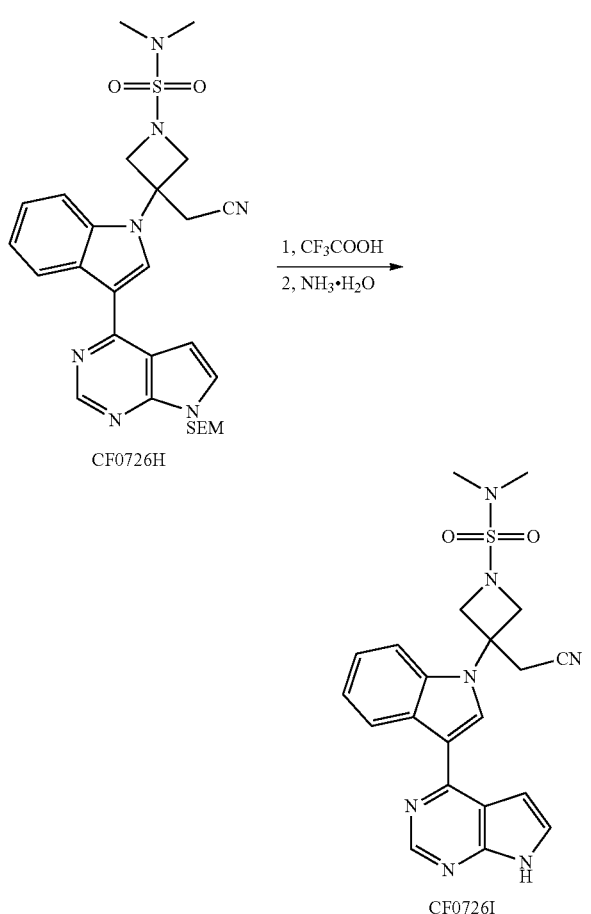

Dissolving raw material CF0726F (0.1 g, 0.000177 mol) into DCM (5 mL), adding TFA (2 mL), performing room-temperature stirring and LCMS tracking, spinning it dry after the reaction, adding DCM and re-spinning it dry twice to remove excess acid, adding methyl alcohol for dissolution, adding saturated ammonia (10 mL), performing room-temperature stirring and separating solid out, performing LCMS tracking, adding ice to cool it after the reaction, filtering and drying to obtain 70 mg of faint yellow product.

MS ES+: 436.2

1H-NMR (400 MHz, DMSO); δ (ppm): 7.09-8.80 (m, 8H, aromatic —H), 4.60 (d, 2H, J=4.4 Hz, —N—CH2-), 4.47 (d, 2H, J=4.4 Hz, —N—CH2-), 3.63 (s, 2H, —CH2-CN), 2.82 (s, 3H, —N—CH3)

The compound of Examples 8-10 can be prepared by the preparation method similar to Example 7:

Example 8

2-(3-(3-(7H-pyrrole[2,3-d]pyrimidine-4-yl)-1H-indole-1-yl)-3-(ethyl cyano)-N,N-methyl ethyl azetidine-1-sulfanilamide.

Example 9

2-(3-(3-(7H-pyrrole[2,3-d]pyrimidine-4-yl)-1H-indole-1-yl)-3-(ethyl cyano)-N,N-diethyl azetidine-1-sulfanilamide.

Example 10

2-(3-(3-(7H-pyrrole[2,3-d]pyrimidine-4-yl)-1H-indole-1-yl)-3-(ethyl cyano)-pyrrolidine-1-sulfanilamide.

Example 11

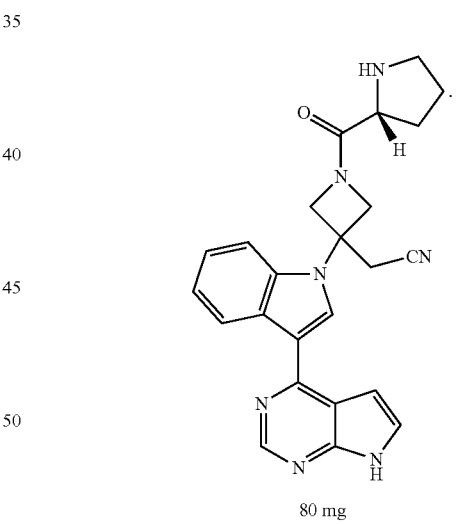

80 mg

Preparation Method:

1) Step 1: Synthesis of CF0726A

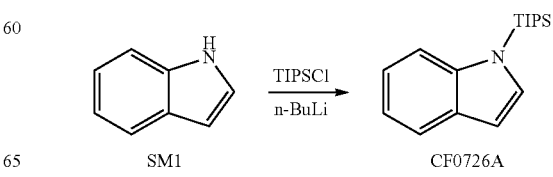

Dissolving 1 (24 g, 0.205 mol) in THF (240 mL), cooling to about −78° C. under the protection of nitrogen, slowly dropwise adding n-BuLi (106 mL, 0.265 mol, 1.3 eq), and keeping and stirring for 1 h after addition. Slowly dropwise adding TIPSCl (52.8 g, 0.274 mol, 1.3 eq), keeping temperature at about −78° C., and then keeping and reacting for 1 h after addition, performing TLC tracking reaction, adding water for quenching after the reaction, using EA for extraction, spinning it dry to obtain 73 g of yellow oily crude product, and directly carrying out the next reaction without purification.

2) Step 2: Synthesis of CF0726B

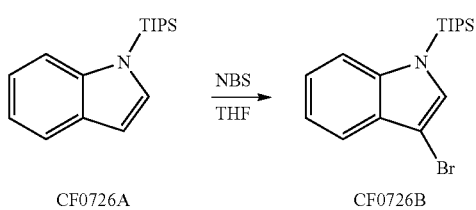

Dissolving CF0726A (36.5 g, P=90%, 0.121 mol) in THF (365 mL), cooling to about −78° C., slowly adding NBS (23 g, 0.129 mol, 1.07 eq), keeping for 1 h after addition and performing LCMS tracking reaction. Adding water for quenching after the reaction, using EA for extraction, spinning it dry to obtain 50 g of faint yellow oily crude product and making alkaline $Al_2O_3$ pass the column to obtain 21.4 g of white solid product (PE eluted).

3) Step 3: Synthesis of CF0726C

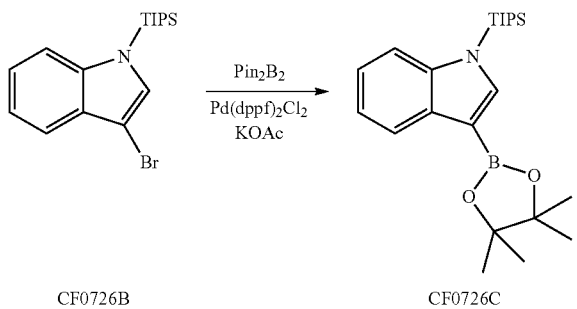

Placing CF0726B (12.5 g, P91.7%, 0.0327 mol), Pin2B2 (41.5 g, 0.163 mol, 5 eq), KOAc (16 g, 0.163 mol, 5 eq), Pd(dppf)Cl2 (2 g, 0.0026 mol, 0.08 eq) in a 250 mL three-necked flask, vacuumizing with an oil pump for 30 min, adding dioxane (140 mL) and reacting overnight at 80-95° C. under the protection of nitrogen. Performing LCMS tracking, adding DCM for dilution after the reaction, filtering and removing insoluble substances, using $H_2O$/DCM for extraction, and spinning the organic phase dry to obtain 10 g of faint yellow oily crude product (including approximate 30% of product, Pin2B2 and CF0726A).

4) Step 4: Synthesis of CF0726E

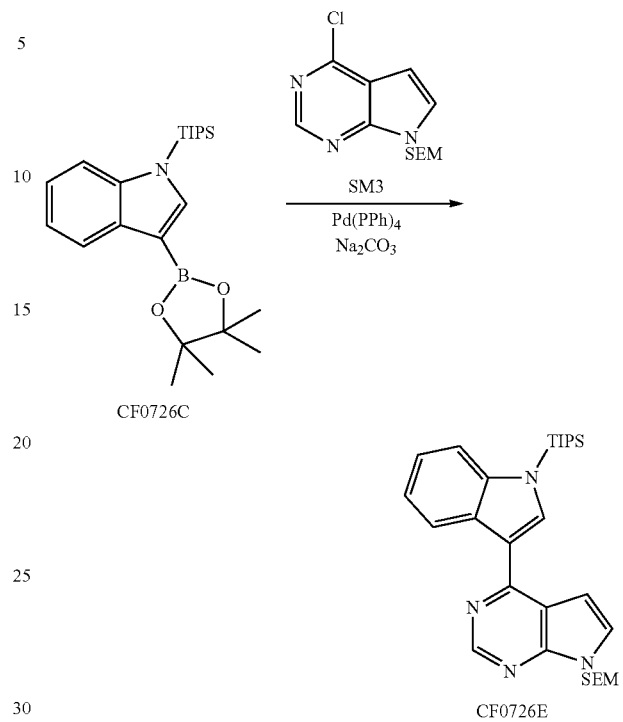

Dissolving raw material CF0726C (10 g, P30%, 0.0075 mol), SM3 (2.1 g, 0.0074 mol, 1 eq), $Na_2CO_3$ (1.59 g, 0.015 mol, 2 eq) and $Pd(PPh_3)_4$ (0.26 g, 0.000225 mol, 0.03 eq) in ethanol/water (80 mL, 1:1), performing the reaction at about 80° C., performing LCMS tracking, refilling SM3 until the raw material disappears, adding DCM for dilution after the reaction, filtering and removing insoluble substances, using $H_2O$/DCM for extraction, spinning the organic phase dry to obtain 8.5 g of yellow oily crude product, and directly performing the next reaction without purification (containing about 21.6% of product).

5) Step 5: Synthesis of CF0726F

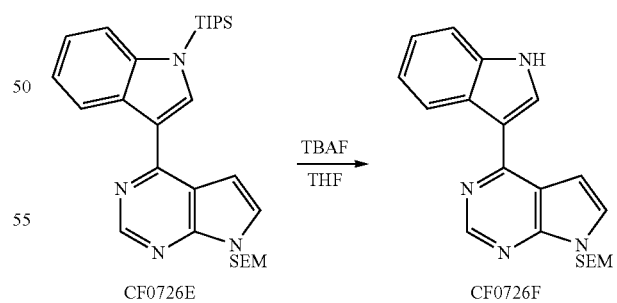

Dissolving raw material CF0726E (8.5 g, P21.6%, 0.0035 mol) and TBAF (4.3 g, 0.0165 mol, 4.7 eq) in THF (85 mL), performing room-temperature stirring and LCMS tracking, spinning it dry after the reaction, adding $H_2O$/EA for extraction, spinning the organic phase dry, making it pass the column to obtain white solid product (PE/EA=1:4 eluted) so as to obtain 1 g of white solid product.

6) Step 6: Synthesis of SM2

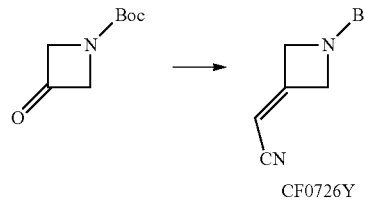

CF0726Y

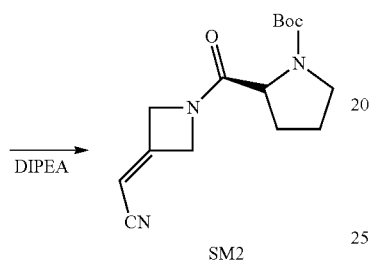

SM2

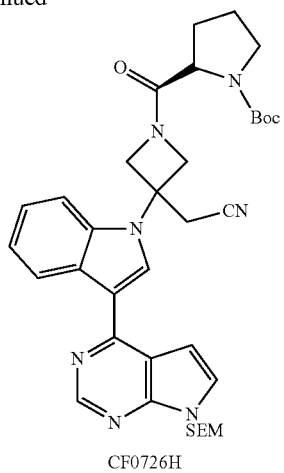

CF0726H

1, Dissolving cyanomethyl diethyl phosphate in THF (75 mL), cooling to −7−−5° C. under the protection of nitrogen, dropwise adding potassium tert-butoxide/THF (3.6 g is dissolved in 35 mL of THF), keeping for 3 h after addition, dropwise adding 1-Boc-3-azetidinone/THF solution (5 g is dissolved in 15 mL of THF), keeping for 1 h and then stirring overnight at room temperature, using EA/H2O for extraction after adding water for quenching, spinning it dry to obtain 8 g of crude product, and putting the product into the column to obtain 4.3 g of white solid product CF0726Y.

2, Dissolving CF0726Y (0.5 g, 0.0026 mol) in dioxane solution (10 mL) of saturated hydrogen chloride, clearly dissolving it and separating white solid out, spinning solvent dry after raw material disappears, adding DCM (10 mL) to dissolve it, and then adding TEA (1.51 g, 14.9 mmol, 5.8 eq), stirring for 10 min, adding EDCI (0.62 g, 3.2 mmol, 1.25 eq), HOBT (0.43 g, 3.2 mmol, 1.25 eq), stirring for 15 min and then adding N-Boc-L-proline (0.56 g, 2.6 mmol, 1.0 eq), performing room-temperature stirring overnight. Performing LCMS tracking, adding DCM/H2O for extraction after the reaction, washing it with saturated NaHCO3 solution and spinning it dry to obtain brown oily substance (0.7 g).

7) Step 7: Synthesis of CF0726H

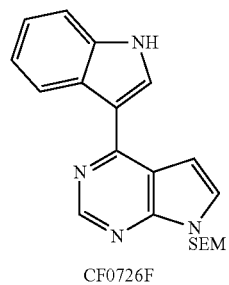

CF0726F $\xrightarrow{\text{DBU}}_{\text{SM2}}$

Dissolving raw material CF0726F (0.1 g, 0.00027 mol) in acetonitrile (5 mL), adding SM2 (0.1 g, 0.00036 mol, 1.3 eq) and DBU (0.1 g, 0.00066 mol, 2.4 eq), performing room-temperature stirring overnight, spinning it dry after the reaction, using H2O/EA for extraction, spinning the organic phase dry and making it pass the column to obtain 0.2 g of product (PE/EA=3:1-1:1).

8) Step 8: Synthesis of CF0726L

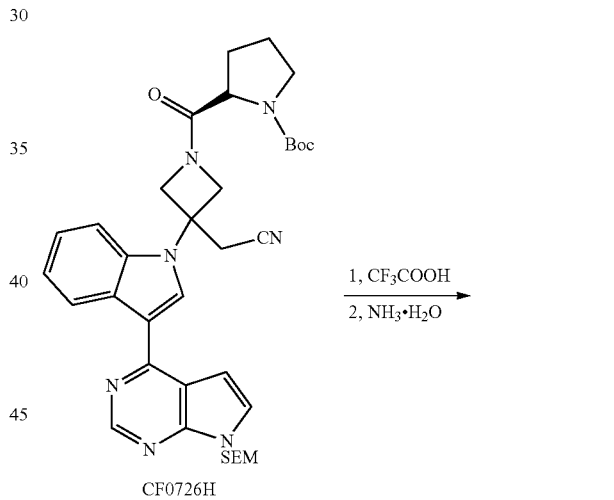

CF0726H

1, CF3COOH
2, NH3·H2O

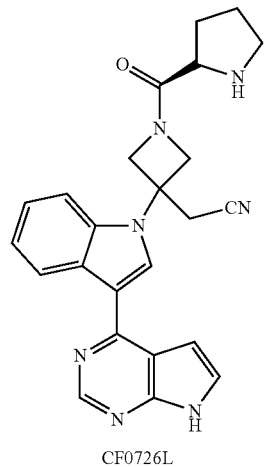

CF0726L

Dissolving raw material CF0726F (0.2 g, 0.0003 mol) into DCM (10 mL), adding TFA (4 mL), performing room-temperature stirring and LCMS tracking, spinning it dry after the reaction, adding DCM and re-spinning it dry twice to remove excess acid, adding methyl alcohol (10 mL) for dissolution, adding saturated ammonia (10 mL), performing room-temperature stirring and separating a little amount of solid out, performing LCMS tracking, spinning and removing methanol after the reaction, spinning it dry to obtain yellow product, and sending it to the preparation column for purification to obtain 80 mg of faint yellow product.

MS ES+: 426.2;

1H-NMR (400 MHz, DMSO); δ (ppm): 7.28-8.80 (m, 8H, aromatic —H), 4.54-4.69 (m, 4H, —N—CH2-*2), 4.49 (d, 2H, J=4.6 Hz, —N—CH2-), 3.61 (s, 2H, —CH2-CN), 3.60 (s, 1H, —CH—N), 3.59 (m, 2H, —CH—N), 1.74-1.78 (m, 4H, —CH2-CH2-)

The compound of Examples 12-19 can be prepared by the preparation method similar to Example 11:

Example 12

2-(3-(3-(7H-pyrrole[2,3-d]pyrimidine-4-yl)-1H-indole-1-yl)-1-(piperidine-2-carbonyl)zetidine-3-yl)acetonitrile.

Example 13

2-(3-(3-(7H-pyrrole[2,3-d]pyrimidine-4-yl)-1H-indole-1-yl)-1-(azacycloheptane-2-carbonyl)azetidine-3-yl)acetonitrile.

Example 14

2-(3-(3-(7H-pyrrole[2,3-d]pyrimidine-4-yl)-1H-indole-1-yl)-1-(tetrahydrofuran-2-carbonyl)azetidine-3-yl)acetonitrile.

Example 15

2-(3-(3-(7H-pyrrole[2,3-d]pyrimidine-4-yl)-1H-indole-1-yl)-1-(tetrahydropyridine-2-carbonyl)azetidine-3-yl)acetonitrile.

Example 16

2-(3-(3-(7H-pyrrole[2,3-d]pyrimidine-4-yl)-1H-indole-1-yl)-1-(oxacycloheptane-2-carbonyl)azetidine-3-yl)acetonitrile.

Example 17

2-(3-(3-(7H-pyrrole[2,3-d]pyrimidine-4-yl)-1H-indole-1-yl)-1-(tetrahydrothiophene-2-carbonyl)azetidine-3-yl)acetonitrile.

Example 18

2-(3-(3-(7H-pyrrole[2,3-d]pyrimidine-4-yl)-1H-indole-1-yl)-1-(tetrahydrothiapyran-2-carbonyl)azetidine-3-yl)acetonitrile.

Example 19

2-(3-(3-(7H-pyrrole[2,3-d]pyrimidine-4-yl)-1H-indole-1-yl)-1-(thiacycloheptane-2-carbonyl)azetidine-3-yl)acetonitrile.

Example 20

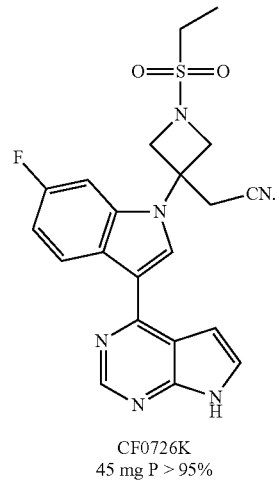 [SMILES: CCS(=O)(=O)N1CC(CC#N)(n2cc(-c3ncnc4[nH]ccc34)c3ccc(F)cc32)C1]

CF0726K
45 mg P > 95%

Preparation Method:
1) Step 1: Synthesis of CF0726A

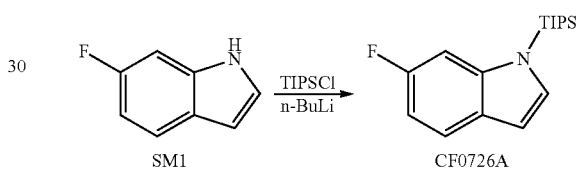

Dissolving raw material SM1 (10 g, 0.074 mol) in THF (100 mL), cooling to about −78° C. under the protection of nitrogen, slowly dropwise adding n-BuLi (37.7 mL, 0.09 mol, 1.2 eq), and keeping and stirring for 1 h after addition. Slowly dropwise adding TIPSCl (17.2 g, 0.089 mol, 1.2 eq), keeping temperature at about −78° C., and then keeping and reacting for 1 h after addition, performing TLC tracking reaction, adding water for quenching after the reaction, using EA for extraction, spinning it dry to obtain 17.3 g of yellow oily crude product, and directly carrying out the next reaction without purification.

2) Step 2: Synthesis of CF0726B

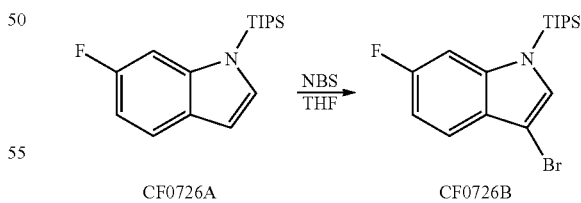

Dissolving CF0726A (17 g, P=79%, 0.046 mol) in THF (170 mL), cooling to about −78° C., slowly adding NBS (8.2 g, 0.046 mol, 1 eq), keeping for 1 h after addition, performing LCMS tracking reaction, refilling NBS until the raw material disappears. Adding water for quenching after the reaction, using EA for extraction, spinning it dry to obtain 36 g of red crude product and making alkaline Al2O3 pass the column to obtain 36 g of white solid product (PE eluted, overweight).

3) Step 3: Synthesis of CF0726C

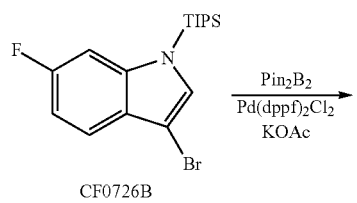

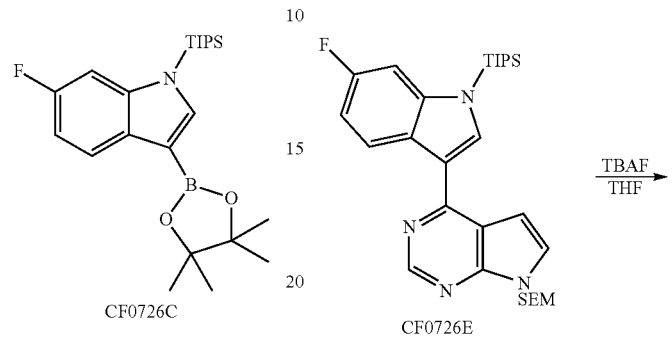

Placing CF0726B (14 g, P979, 0.038 mol), Pin2B2 (48.2 g, 0.19 mol, 5 eq), KOAc (18.6 g, 0.19 mol, 5 eq), Pd (dppf) Cl$_2$ (3 g, 0.0039 mol, 0.1 eq) in a 250 mL three-necked flask, vacuumizing with an oil pump for 30 min, adding dioxane (140 mL) and reacting overnight at 80-95° C. under the protection of nitrogen. Performing LCMS tracking, adding DCM for dilution after the reaction, filtering and removing insoluble substances, using H$_2$O/DCM for extraction, spinning the organic phase dry to obtain 29 g of faint yellow oily crude product (including approximate 32% of product, Pin2B2 and CF0726A).

4) Step 4: Synthesis of CF0726E

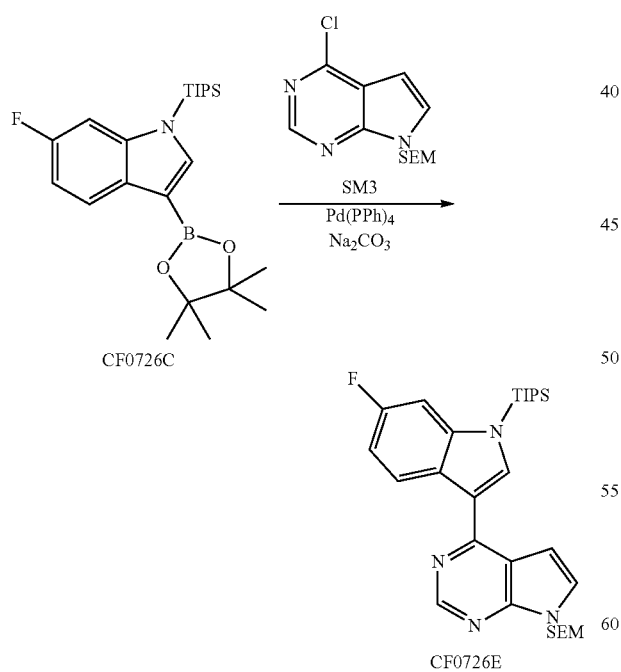

Dissolving raw material CF0726C (2 g, P32%, 0.0015 mol), SM3 (0.6 g, 0.0021 mol, 1.4 eq), Na$_2$CO$_3$ (0.44 g, 0.041 mol, 2.7 eq) and Pd(PPh$_3$)$_4$ (0.06 g, 0.00005 mol, 0.03 eq) in ethanol/water (20 mL, 1:1), performing the reaction at about 80° C., performing LCMS tracking, refilling SM3 until the raw material disappears, adding DCM for dilution after the reaction, filtering and removing insoluble substances, using H$_2$O/DCM for extraction, spinning the organic phase dry to obtain 1.7 g of yellow oily crude product, and directly performing the next reaction without purification (containing about 11.5% of product).

5) Step 5: Synthesis of CF0726F

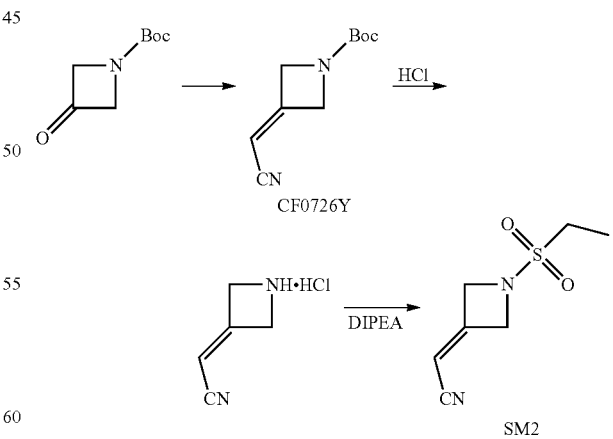

Dissolving raw material CF0726E (1.7 g, P11.5%, 0.0003 mol) and TBAF (0.82 g, 0.003 mol, 10 eq) in THF (17 mL), performing room-temperature stirring and LCMS tracking, spinning it dry after the reaction, adding H$_2$O/EA for extraction, spinning the organic phase dry, making it pass the column to obtain white solid product (PE/EA=1:4 eluted) so as to obtain 0.2 g of white solid product.

6) Step 6: Synthesis of SM2

1, Dissolving cyanomethyl diethyl phosphate in THF (75 mL), cooling to −7-−5° C. under the protection of nitrogen, dropwise adding potassium tert-butoxide/THF (3.6 g is dissolved in 35 mL of THF), keeping for 3 h after addition, dropwise adding 1-Boc-3-azetidinone/THF solution (5 g is dissolved in 15 mL of THF), keeping for 1 h and then stirring overnight at room temperature, using EA/H2O for extraction after adding water for quenching, spinning it dry to obtain 8 g of crude product, and putting the product into the column to obtain 4.3 g of white solid product CF0726Y.

2, Dissolving raw material CF0726Y (0.4 g, 0.0021 mol) in dioxane solution (10 mL) of saturated hydrogen chloride, clearly dissolving it and separating white solid out, spinning solvent dry after raw material disappears, adding THF (10 mL) to dissolve it, then dropwise adding DIPEA (0.8 g, 6.18 mmol, 3 eq), stirring for 10 min, dropwise adding ethylsulfonyl chloride (0.32 g, 0.0025 mol, 1.2 eq), performing room-temperature stirring and LCMS tracking, spinning it dry after the reaction, using EA/H$_2$O for extraction, washing it once with NaHCO$_3$ and washing with saturated saline solution, spinning it dry to obtain 0.3 g of yellow oily crude product.

7) Step 7: Synthesis of CF0726H

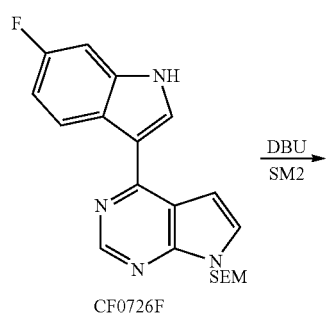

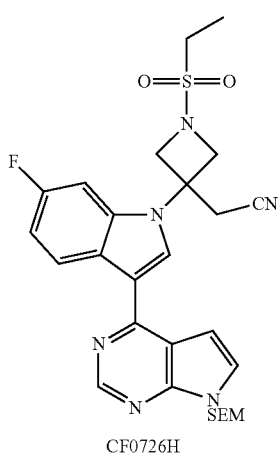

Dissolving raw material CF0726F (0.2 g, 0.00052 mol) in acetonitrile (5 mL), adding SM2 (0.2 g, 0.00108 mol, 2.1 eq) and DBU (0.2 g, 0.00132 mol, 2.5 eq), performing room-temperature stirring overnight, spinning it dry after the reaction, using H$_2$O/EA for extraction, spinning the organic phase dry and making it pass the column to obtain 0.1 g of product (PE/EA=3:1-1:1).

8) Step 8: Synthesis of CF0726K

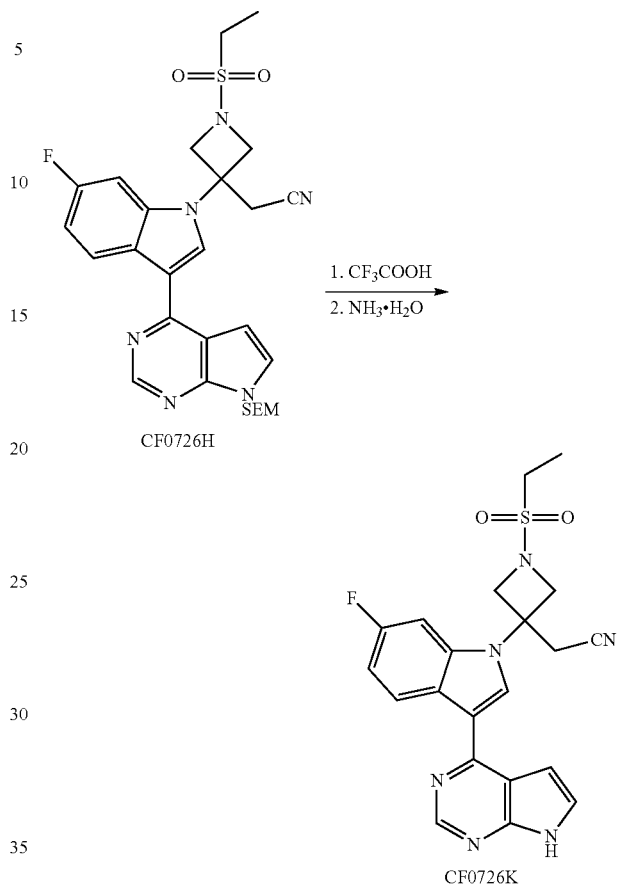

Dissolving raw material CF0726F (0.1 g, 0.00018 mol) into DCM (5 mL), adding TFA (2 mL), performing room-temperature stirring and LCMS tracking, spinning it dry after the reaction, adding DCM and re-spinning it dry twice to remove excess acid, adding methyl alcohol for dissolution, adding saturated ammonia (10 mL), performing room-temperature stirring and separating solid out, performing LCMS tracking, adding ice to cool it after the reaction, filtering and drying to obtain 50 mg of faint yellow product.

MS ES+: 439.2

$^1$H-NMR (400 MHz, DMSO); δ (ppm): 7.11-8.80 (m, 7H, aromatic —H), 4.72 (d, 2H, J=4.4 Hz, —N—CH$_2$—), 4.49 (d, 2H, J=4.4 Hz, —N—CH$_2$—), 3.63 (s, 2H, —CH$_2$—CN), 3.24 (q, J=7.4 Hz, 2H, S—CH$_2$—CH$_3$), 1.24 (t, J=3.6 Hz, 3H, S—CH$_2$—CH$_3$)

The compound of Examples 21-61 can be prepared by the preparation method similar to Example 20:

Example 21

2-(1-(methyl sulfonyl)-3-(6-fluoro-3-(7H-pyrrole[2,3-d]pyrimidine-4-yl)-1H-indole-1-yl)azetidine-3-yl)acetonitrile.

Example 22

2-(1-(propyl sulfonyl)-3-(6-fluoro-3-(7H-pyrrole[2,3-d]pyrimidine-4-yl)-1H-indole-1-yl)azetidine-3-yl)acetonitrile.

Example 23

2-(1-(isopropyl sulfonyl)-3-(6-fluoro-3-(7H-pyrrole[2,3-d]pyrimidine-4-yl)-1H-indole-1-yl)azetidine-3-yl)acetonitrile.

Example 24

2-(1-(cyclopropyl sulfonyl)-3-(6-fluoro-3-(7H-pyrrole[2,3-d]pyrimidine-4-yl)-1H-indole-1-yl)azetidine-3-yl)acetonitrile

Example 25

2-(1-(methyl sulfonyl)-3-(6-chloro-3-(7H-pyrrole[2,3-d]pyrimidine-4-yl)-1H-indole-1-yl)azetidine-3-yl)acetonitrile.

Example 26

2-(1-(ethyl sulfonyl)-3-(6-chloro-3-(7H-pyrrole[2,3-d]pyrimidine-4-yl)-1H-indole-1-yl)azetidine-3-yl)acetonitrile.

Example 27

2-(1-(propyl sulfonyl)-3-(6-chloro-3-(7H-pyrrole[2,3-d]pyrimidine-4-yl)-1H-indole-1-yl)azetidine-3-yl)acetonitrile.

Example 28

2-(1-(isopropyl sulfonyl)-3-(6-chloro-3-(7H-pyrrole[2,3-d]pyrimidine-4-yl)-1H-indole-1-yl)azetidine-3-yl)acetonitrile.

Example 29

2-(1-(cyclopropyl sulfonyl)-3-(6-chloro-3-(7H-pyrrole[2,3-d]pyrimidine-4-yl)-1H-indole-1-yl)azetidine-3-yl)acetonitrile.

Example 30

2-(1-(methyl sulfonyl)-3-(6-bromo-3-(7H-pyrrole[2,3-d]pyrimidine-4-yl)-1H-indole-1-yl)azetidine-3-yl)acetonitrile.

Example 31

2-(1-(ethyl sulfonyl)-3-(6-bromo-3-(7H-pyrrole[2,3-d]pyrimidine-4-yl)-1H-indole-1-yl)azetidine-3-yl)acetonitrile.

Example 32

2-(1-(methyl sulfonyl)-3-(5,6-difluoro-3-(7H-pyrrole[2,3-d]pyrimidine-4-yl)-1H-indole-1-yl)azetidine-3-yl)acetonitrile.

Example 33

2-(1-(ethyl sulfonyl)-3-(5,6-difluoro-3-(7H-pyrrole[2,3-d]pyrimidine-4-yl)-1H-indole-1-yl)azetidine-3-yl)acetonitrile.

Example 34

2-(1-(propyl sulfonyl)-3-(5,6-difluoro-3-(7H-pyrrole[2,3-d]pyrimidine-4-yl)-1H-indole-1-yl)azetidine-3-yl)acetonitrile.

Example 35

2-(1-(cyclopropyl sulfonyl)-3-(5,6-difluoro-3-(7H-pyrrole[2,3-d]pyrimidine-4-yl)-1H-indole-1-yl)azetidine-3-yl)acetonitrile.

Example 36

2-(1-(methyl sulfonyl)-3-(6,7-difluoro-3-(7H-pyrrole[2,3-d]pyrimidine-4-yl)-1H-indole-1-yl)azetidine-3-yl)acetonitrile.

Example 37

2-(1-(ethyl sulfonyl)-3-(6,7-difluoro-3-(7H-pyrrole[2,3-d]pyrimidine-4-yl)-1H-indole-1-yl)azetidine-3-yl)acetonitrile.

Example 38

2-(1-(propyl sulfonyl)-3-(6,7-difluoro-3-(7H-pyrrole[2,3-d]pyrimidine-4-yl)-1H-indole-1-yl)azetidine-3-yl)acetonitrile.

Example 39

2-(1-(isopropyl sulfonyl)-3-(6,7-difluoro-3-(7H-pyrrole[2,3-d]pyrimidine-4-yl)-1H-indole-1-yl)azetidine-3-yl)acetonitrile.

Example 40

2-(1-(cyclopropyl sulfonyl)-3-(6,7-difluoro-3-(7H-pyrrole[2,3-d]pyrimidine-4-yl)-1H-indole-1-yl)azetidine-3-yl)acetonitrile.

Example 41

2-(1-(methyl sulfonyl)-3-(6,8-difluoro-3-(7H-pyrrole[2,3-d]pyrimidine-4-yl)-1H-indole-1-yl)azetidine-3-yl)acetonitrile.

Example 42

2-(1-(ethyl sulfonyl)-3-(6,8-difluoro-3-(7H-pyrrole[2,3-d]pyrimidine-4-yl)-1H-indole-1-yl)azetidine-3-yl)acetonitrile.

Example 43

2-(1-(propyl sulfonyl)-3-(6,8-difluoro-3-(7H-pyrrole[2,3-d]pyrimidine-4-yl)-1H-indole-1-yl)azetidine-3-yl)acetonitrile.

Example 44

2-(1-(isopropyl sulfonyl)-3-(6,8-difluoro-3-(7H-pyrrole[2,3-d]pyrimidine-4-yl)-1H-indole-1-yl)azetidine-3-yl)acetonitrile.

Example 45

2-(1-(cyclopropyl sulfonyl)-3-(6,8-difluoro-3-(7H-pyrrole[2,3-d]pyrimidine-4-yl)-1H-indole-1-yl)azetidine-3-yl)acetonitrile.

Example 46

2-(1-(ethyl sulfonyl)-3-(5,7-difluoro-3-(7H-pyrrole[2,3-d]pyrimidine-4-yl)-1H-indole-1-yl)azetidine-3-yl)acetonitrile.

Example 47

2-(1-(ethyl sulfonyl)-3-(5,7-difluoro-3-(7H-pyrrole[2,3-d]pyrimidine-4-yl)-1H-indole-1-yl)azetidine-3-yl)acetonitrile.

Example 48

2-(1-(ethyl sulfonyl)-3-(5,8-difluoro-3-(7H-pyrrole[2,3-d]pyrimidine-4-yl)-1H-indole-1-yl)azetidine-3-yl)acetonitrile.

Example 49

2-(1-(ethyl sulfonyl)-3-(7,8-difluoro-3-(7H-pyrrole[2,3-d]pyrimidine-4-yl)-1H-indole-1-yl)azetidine-3-yl)acetonitrile.

Example 50

2-(1-(ethyl sulfonyl)-3-(6-cyano-3-(7H-pyrrole[2,3-d]pyrimidine-4-yl)-1H-indole-1-yl)azetidine-3-yl)acetonitrile.

Example 51

2-(1-(ethyl sulfonyl)-3-(6-ethyl cyano-3-(7H-pyrrole[2,3-d]pyrimidine-4-yl)-1H-indole-1-yl)azetidine-3-yl)acetonitrile.

Example 52

2-(1-(ethyl sulfonyl)-3-(6-trifluoromethyl-3-(7H-pyrrole[2,3-d]pyrimidine-4-yl)-1H-indole-1-yl)azetidine-3-yl)acetonitrile.

Example 53

2-(1-(ethyl sulfonyl)-3-(6-trifluoroethyl-3-(7H-pyrrole[2,3-d]pyrimidine-4-yl)-1H-indole-1-yl)azetidine-3-yl)acetonitrile.

Example 54

2-(1-(ethyl sulfonyl)-3-(6-methyl-3-(7H-pyrrole[2,3-d]pyrimidine-4-yl)-1H-indole-1-yl)azetidine-3-yl)acetonitrile.

Example 55

2-(1-(ethyl sulfonyl)-3-(6-ethyl-3-(7H-pyrrole[2,3-d]pyrimidine-4-yl)-1H-indole-1-yl)azetidine-3-yl)acetonitrile.

Example 56

2-(1-(ethyl sulfonyl)-3-(6-propyl-3-(7H-pyrrole[2,3-d]pyrimidine-4-yl)-1H-indole-1-yl)azetidine-3-yl)acetonitrile.

Example 57

2-(1-(ethyl sulfonyl)-3-(6-isopropyl-3-(7H-pyrrole[2,3-d]pyrimidine-4-yl)-1H-indole-1-yl)azetidine-3-yl)acetonitrile.

Example 58

2-(1-(ethyl sulfonyl)-3-(6-methoxyl-3-(7H-pyrrole[2,3-d]pyrimidine-4-yl)-1H-indole-1-yl)azetidine-3-yl)acetonitrile.

Example 59

2-(1-(ethyl sulfonyl)-3-(6-ethoxyl-3-(7H-pyrrole[2,3-d]pyrimidine-4-yl)-1H-indole-1-yl)azetidine-3-yl)acetonitrile.

Example 60

2-(1-(ethyl sulfonyl)-3-(6-propoxyl-3-(7H-pyrrole[2,3-d]pyrimidine-4-yl)-1H-indole-1-yl)azetidine-3-yl)acetonitrile.

Example 61

2-(1-(ethyl sulfonyl)-3-(6-isopropoxyl-3-(7H-pyrrole[2,3-d]pyrimidine-4-yl)-1H-indole-1-yl)azetidine-3-yl)acetonitrile.

Example 62

2-(1-(ethyl sulfonyl)-3-(5-fluoro-3-(7H-pyrrole[2,3-d]pyrimidine-4-yl)-1H-indole-1-yl)azetidine-3-yl)acetonitrile.

Example 63

2-(1-(ethyl sulfonyl)-3-(5-trifluoromethyl-3-(7H-pyrrole[2,3-d]pyrimidine-4-yl)-1H-indole-1-yl)azetidine-3-yl)acetonitrile.

Example 64

2-(1-(ethyl sulfonyl)-3-(5-methoxyl-3-(7H-pyrrole[2,3-d]pyrimidine-4-yl)-1H-indole-1-yl)azetidine-3-yl)acetonitrile.

Example 65: Synthesis of CF0726J Trifluoroacetate

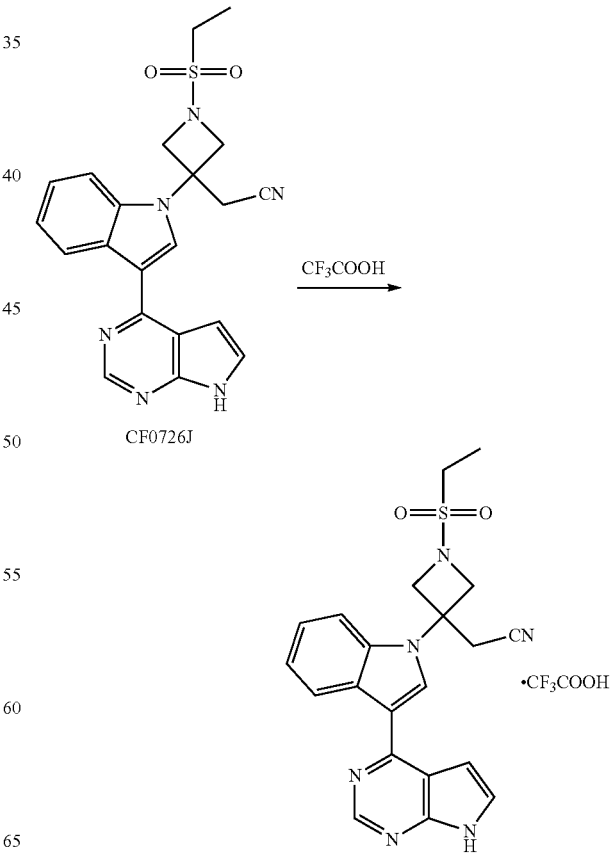

Dissolving CF0726J (0.1 g, 0.00035 mol) in DCM (5 mL), adding TFA (2 mL), heating up to 45° C., performing room-temperature stirring for 1 h, adding DCM and spinning it dry twice to remove excess acid, adding the mixed solvent of acetone:methyl alcohol:water for recrystallization to obtain 53 mg of CF0726J trifluoroacetate.

Example 66: Synthesis of CF0726K Phosphate

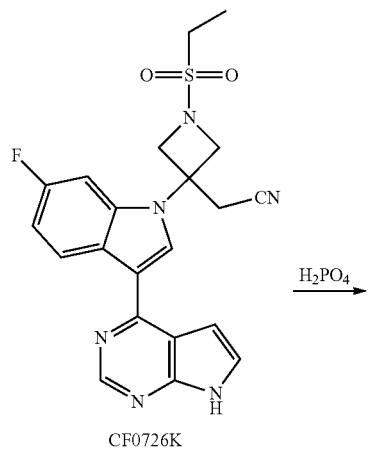

CF0726K $\xrightarrow{H_2PO_4}$

-continued

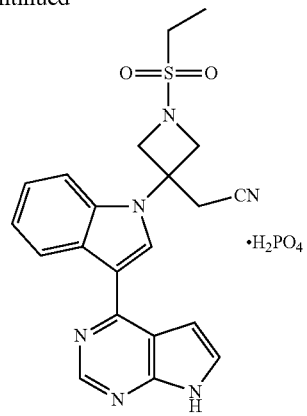

$\cdot H_3PO_4$

Dissolving CF0726K (0.1 g, 0.00023 mol) in DCM (5 mL), adding phosphoric acid (1.5 mL), heating up to 40° C., performing room-temperature stirring for 2 h, adding DCM and spinning it dry twice to remove excess acid, adding the mixed solvent of acetone:methyl alcohol:water for recrystallization to obtain 38 mg of CF0726K trifluoroacetate.

Example 67

Using in-vivo Caliper Mobility Shift Assay method to study and detect the effect of the compounds listed as below of the invention on Janus-activated kinase inhibitor by Km value under different concentrations of triphosadenine (ATP). It is found that the compound of the invention has obvious inhibition on JAK-STAT path. Partial data are shown as follows:

| Example No. | Chemical name | IC50 (nM) JAK1 | JAK2 | JAK3 |
|---|---|---|---|---|
| 1 | 2-(3-(3-(7H-pyrrole[2,3-d]pyrimidine-4-yl)-1H-indole-1-yl)-1-(ethyl sulfonyl)azetidine-3-yl)acetonitrile | 11 | 1.1 | 100 |
| 2 | 2-(3-(3-(7H-pyrrole[2,3-d]pyrimidine-4-yl)-1H-indole-1-yl)-1-(methyl sulfonyl)azetidine-3-yl)acetonitrile | 8 | 0.9 | 128 |
| 6 | 2-(3-(3-(7H-pyrrole[2,3-d]pyrimidine-4-yl)-1H-indole-1-yl)-1-(butyl sulfonyl)azetidine-3-yl)acetonitrile | 22 | 7.1 | 200 |
| 7 | 2-(3-(3-(7H-pyrrole[2,3-d]pyrimidine-4-yl)-1H-indole-1-yl)-3-(ethyl cyano)-N,N-dimethyl azetidine-1-sulfanilamide | 15 | 1.5 | 116 |
| 10 | 2-(3-(3-(7H-pyrrole[2,3-d]pyrimidine-4-yl)-1H-indole-1-yl)-3-(ethyl cyano)-pyrrolidine-1-sulfanilamide | 7 | 3.5 | 67 |
| 11 | 2-(3-(3-(7H-pyrrole[2,3-d]pyrimidine-4-yl)-1H-indole-1-yl)-1-(pyrrolidine-2-carbonyl)azetidine-3-yl)acetonitrile | 300 | 692 | 521 |
| 20 | 2-(1-(ethyl sulfonyl)-3-(6-fluoro-3-(7H-pyrrole[2,3-d]pyrimidine-4-yl)-1H-indole-1-yl)azetidine-3-yl)acetonitrile | 0.5 | 0.61 | 28 |
| 26 | 2-(1-(ethyl sulfonyl)-3-(6-chloro-3-(7H-pyrrole[2,3-d]pyrimidine-4-yl)-1H-indole-1-yl)azetidine-3-yl)acetonitrile | 3.5 | 0.72 | 34 |
| 28 | 2-(1-(isopropyl sulfonyl)-3-(6-chloro-3-(7H-pyrrole[2,3-d]pyrimidine-4-yl)-1H-indole-1-yl)azetidine-3-yl)acetonitrile | 6.5 | 2.4 | 64 |
| 31 | 2-(1-(ethyl sulfonyl)-3-(6-bromo-3-(7H-pyrrole[2,3-d]pyrimidine-4-yl)-1H-indole-1-yl)azetidine-3-yl)acetonitrile | 3.5 | 8.3 | 21 |
| 32 | 2-(1-(methyl sulfonyl)-3-(5,6-difluoro-3-(7H-pyrrole[2,3-d]pyrimidine-4-yl)-1H-indole-1-yl)azetidine-3-yl)acetonitrile | 4.5 | 6.3 | 124 |
| 37 | 2-(1-(ethyl sulfonyl)-3-(6,7-difluoro-3-(7H-pyrrole[2,3-d]pyrimidine-4-yl)-1H-indole-1-yl)azetidine-3-yl)acetonitrile | 23.4 | 1.96 | 45 |

| Example No. | Chemical name | IC50 (nM) JAK1 | JAK2 | JAK3 |
|---|---|---|---|---|
| 43 | 2-(1-(propyl sulfonyl)-3-(6,8-difluoro-3-(7H-pyrrole[2,3-d]pyrimidine-4-yl)-1H-indole-1-yl)azetidine-3-yl)acetonitrile | 13.3 | 28.4 | 67 |
| 47 | 2-(1-(ethyl sulfonyl)-3-(5,7-difluoro-3-(7H-pyrrole[2,3-d]pyrimidine-4-yl)-1H-indole-1-yl)azetidine-3-yl)acetonitrile | 30.5 | 11.6 | 58 |
| 48 | 2-(1-(ethyl sulfonyl)-3-(5,8-difluoro-3-(7H-pyrrole[2,3-d]pyrimidine-4-yl)-1H-indole-1-yl)azetidine-3-yl)acetonitrile | 10.5 | 4.6 | 72 |
| 51 | 2-(1-(ethyl sulfonyl)-3-(6-ethyl cyano-3-(7H-pyrrole[2,3-d]pyrimidine-4-yl)-1H-indole-1-yl)azetidine-3-yl)acetonitrile | 45.5 | 41.6 | 172 |
| 53 | 2-(1-(ethyl sulfonyl)-3-(6-trifluoroethyl-3-(7H-pyrrole[2,3-d]pyrimidine-4-yl)-1H-indole-1-yl)azetidine-3-yl)acetonitrile | 5.4 | 1.4 | 17 |
| 54 | 2-(1-(ethyl sulfonyl)-3-(6-methyl-3-(7H-pyrrole[2,3-d]pyrimidine-4-yl)-1H-indole-1-yl)azetidine-3-yl)acetonitrile | 15.2 | 2.5 | 36 |
| 59 | 2-(1-(ethyl sulfonyl)-3-(6-ethyoxyl-3-(7H-pyrrole[2,3-d]pyrimidine-4-yl)-1H-indole-1-yl)azetidine-3-yl)acetonitrile | 25.4 | 2.8 | 90 |
| 62 | 2-(1-(ethyl sulfonyl)-3-(5-fluoro-3-(7H-pyrrole[2,3-d]pyrimidine-4-yl)-1H-indole-1-yl)azetidine-3-yl)acetonitrile | 3.6 | 1.0 | 30 |
| 63 | 2-(1-(ethyl sulfonyl)-3-(5-trifluoromethyl-3-(7H-pyrrole[2,3-d]pyrimidine-4-yl)-1H-indole-1-yl)azetidine-3-yl)acetonitrile | 7.9 | 2.4 | 232 |
| 64 | 2-(1-(ethyl sulfonyl)-3-(5-methoxyl-3-(7H-pyrrole[2,3-d]pyrimidine-4-yl)-1H-indole-1-yl)azetidine-3-yl)acetonitrile | 23 | 2.9 | 262 |
| Reference example | JAK inhibitor Baricitinib | 2.5 | 0.83 | 32 |

Example 68

Using in-vitro CTLL-2 cells to detect the phosphorylation level of JAK so as to check the inhibition of the following compounds on JAK-STAT, culturing CTLL-2 cells and adding to 6-well plate that each well has $1 \times 10^7$ cells, then adding the compound of the invention and starving for 6 h, adding IL-2 and obtaining the final concentration of 150 U/mL. Incubating for 10 min and collecting cells. Adding cell lysis buffer for cell lysis. Collecting protein to perform WEST-Blot detection, detecting phosphorylated JAK1, the phosphorylation of JAK2 and the phosphorylated STAT5, and obtaining the IC50 value.

| Example No. | Chemical name | IC50 g (nM) JAK1 | JAK2 | STAT5 |
|---|---|---|---|---|
| 1 | 2-(3-(3-(7H-pyrrole[2,3-d]pyrimidine-4-yl)-1H-indole-1-yl)-1-(methyl sulfonyl)azetidine-3-yl)acetonitrile | 26.3 | 18.4 | 125 |
| 2 | 2-(3-(3-(7H-pyrrole[2,3-d]pyrimidine-4-yl)-1H-indole-1-yl)-1-(ethyl sulfonyl)azetidine-3-yl)acetonitrile | | 5.4 | 146 |
| 6 | 2-(3-(3-(7H-pyrrole[2,3-d]pyrimidine-4-yl)-1H-indole-1-yl)-1-(butyl sulfonyl)azetidine-3-yl)acetonitrile | 22 | 8.0 | 322 |
| 7 | 2-(3-(3-(7H-pyrrole[2,3-d]pyrimidine-4-yl)-1H-indole-1-yl)-3-(ethyl cyano)-N,N-dimethyl azetidine-1-sulfanilamide | 45 | 9.6 | 214 |
| 11 | 2-(3-(3-(7H-pyrrole[2,3-d]pyrimidine-4-yl)-1H-indole-1-yl)-1-(pyrrolidine-2-carbonyl)azetidine-3-yl)acetonitrile | 30 | 192 | 692 |
| 20 | 2-(1-(ethyl sulfonyl)-3-(6-fluoro-3-(7H-pyrrole[2,3-d]pyrimidine-4-yl)-1H-indole-1-yl)azetidine-3-yl)acetonitrile | 18.5 | 15.2 | 309 |
| 37 | 2-(1-(ethyl sulfonyl)-3-(6,7-difluoro-3-(7H-pyrrole[2,3-d]pyrimidine-4-yl)-1H-indole-1-yl)azetidine-3-yl)acetonitrile | 12.4 | 7.6 | 124 |
| 62 | 2-(1-(ethyl sulfonyl)-3-(5-fluoro-3-(7H-pyrrole[2,3-d]pyrimidine-4-yl)-1H-indole-1-yl)azetidine-3-yl)acetonitrile | 33.9 | 29.9 | 130 |

-continued

| Example No. | Chemical name | IC50 g (nM) | | |
|---|---|---|---|---|
| | | JAK1 | JAK2 | STAT5 |
| 63 | 2-(1-(ethyl sulfonyl)-3-(5-trifluoromethyl-3-(7H-pyrrole[2,3-d]pyrimidine-4-yl)-1H-indole-1-yl)azetidine-3-yl)acetonitrile | 75.2 | 38.3 | 196 |
| 64 | 2-(1-(ethyl sulfonyl)-3-(5-methoxyl-3-(7H-pyrrole[2,3-d]pyrimidine-4-yl)-1H-indole-1-yl)azetidine-3-yl)acetonitrile | 42.9 | 28.7 | 201 |
| Reference example | JAK inhibitor Baricitinib | 32.4 | 22.6 | 235 |

Example 69

The compound of the invention is used for inhibiting cell proliferation of human lymphocytoma. Spreading the Jurkat cells out for in-vitro cultivation on a 96-well plate with 1500 cells in each well, making the highest concentration of the compound be 50 μM in the cultivation system, and diluting the drug concentration according to 10-time step dilution. After making the compound react for 48 h, adding 10 μl CCk-8 and incubating for 6 h, detecting 450 nM wavelength absorption value by ELIASA. Calculating the inhibition rate of the compound on the growth of tumor cells according to the standard method of National Cancer Institute (NCI): when Ti (culturing the drug group for 48 h, CCK-8 coloring absorption OD value)≥Tz (CCK-8 coloring absorption OD value when culturing the group without drugs), survival rate of tumor cells=[(Ti−Tz)/(C−Tz)]×100, where C is the CCK-8 coloring absorption OD value for the group without drugs after 48 h; when Ti<Tz, survival rate of tumor cells=[(Ti−Tz)/Tz]×100.

and scoring arthritis of the rat 2 weeks after administration. The results show that the product has obvious treatment on the rat with rheumatoid arthritis.

| Compound group | Score of arthritis |
|---|---|
| Control | 1 |
| physiological saline control group | 4 |
| Cyclosporine control group | 2.4 |
| Compound of Example 66 | 1.8 |
| Compound of Example 6 | 2.3 |
| Compound of Example 64 | 2.3 |
| Compound of Example 7 | 2.5 |
| Compound of Example 20 | 1.6 |
| JAK inhibitor Baricitinib | 2.4 |

| Example No. | Chemical name | IC50 (nM) |
|---|---|---|
| 65 | 2-(3-(3-(7H-pyrrole[2,3-d]pyrimidine-4-yl)-1H-indole-1-yl)-1-(methyl sulfonyl)azetidine-3-yl)acetonitrile trifluoroacetate | 120 |
| 6 | 2-(3-(3-(7H-pyrrole[2,3-d]pyrimidine-4-yl)-1H-indole-1-yl)-1-(butyl sulfonyl)azetidine-3-yl)acetonitrile | 458 |
| 7 | 2-(3-(3-(7H-pyrrole[2,3-d]pyrimidine-4-yl)-1H-indole-1-yl)-3-(ethyl cyano)-N,N-dimethyl azetidine-1-sulfanilamide | 123 |
| 20 | 2-(1-(ethyl sulfonyl)-3-(6-fluoro-3-(7H-pyrrole[2,3-d]pyrimidine-4-yl)-1H-indole-1-yl)azetidine-3-yl)acetonitrile | 225 |
| 64 | 2-(1-(ethyl sulfonyl)-3-(5-methoxyl-3-(7H-pyrrole[2,3-d]pyrimidine-4-yl)-1H-indole-1-yl)azetidine-3-yl)acetonitrile. | 136 |
| Reference example | JAK inhibitor Baricitinib | 467 |

Example 70

For the function of the compound inhibiting rheumatoid arthritis, selecting DBA/1J rat, carrying out subcutaneous injection after complete emulsion of 50 ug of bovine Type II collagen and isometric complete Freund's adjuvant (CFA). Strengthening immunization once 21 days after adequate emulsion of 50 ug of same antigen and incomplete Freund's adjuvant (IFA). Starting observation and recording from the 45th day. Using 1-4 scoring method: 1 score, normal; 2 scores, swelling of one joint; 3 scores, swelling of more than one joint but not all joints; 4 scores, severe swelling or stiffness of the whole claw. Adding scores of all claws to obtain the total score of arthritis in rat. Showing successful model establishment when the total joint score of the rat is more than 1. After successfully establishing the model of rat with rheumatoid arthritis, using the compound of the invention to feed the rat by intragastric administration

What is claimed is:
1. A compound of chemical formula I, or optical isomer thereof or a salt thereof,

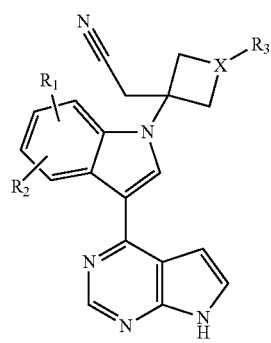

wherein, R1 and R2 are substituents at any position of benzene ring and independently selected from:
hydrogen; any halogen atom;
or —(CH Z)nCN, n=0-3, Z=1-2;
or —(CH Z)nCH3, n=0-3, Z=0-2;
or CYn, n=0-3, Y is any halogen atom;
or —(CH Z)nCYn, n=0-3, Z=1-2, Y is any halogen atom;

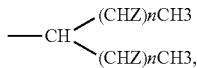

n=0-3, Z=0-2;
or —(CH Z)n, n=0-3, Z=0-2;
or —O(CH Z)n CH3, n=0-3, Z=0-2;
or cycloalkanes of C3-C6; and
R3 is:

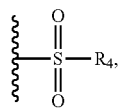

wherein, R4 is selected from hydrogen, alkyl of (C1-C4), alkenyl of (C2-C4), alkynyl of (C2-C4) and cycloalkanes of C3-C7, or

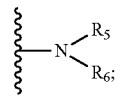

R5 and R6 are selected from hydrogen, alkyl of (C1-C4), alkenyl of (C2-C4), alkynyl of (C2-C4) or cycloalkanes of C3-C7; or R5 and R6 form 4-6 membered rings; R5 and R6 are the same or different;
or, R3 is:

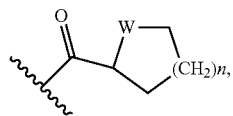

wherein, W is S, N or C, and n is 1-3; and
X is CH or N.

2. A method of preparing the compound of formula I recited in claim 1, comprising the following steps of:
(1) adding amino protecting group to the secondary amine of said compound in compound A structure to obtain compound B;

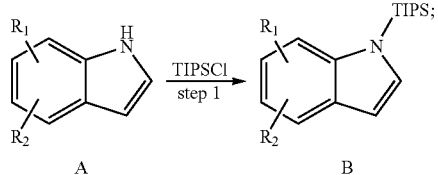

(2) substituting hydrogen of compound B at the position as shown in the following chemical reaction formula by bromine to form compound C;

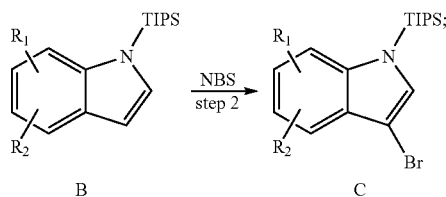

(3) making compound C react with bispinacolatodiboronmin (Pin 2 B 2) to form compound D;

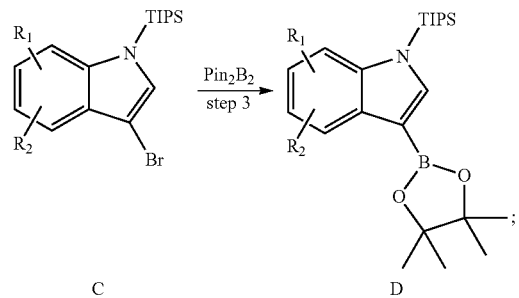

(4) making compound D react with compound E to form compound F under alkaline environment;

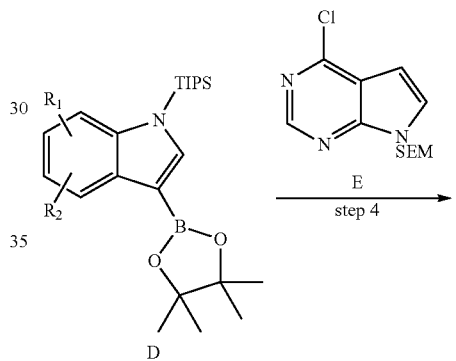

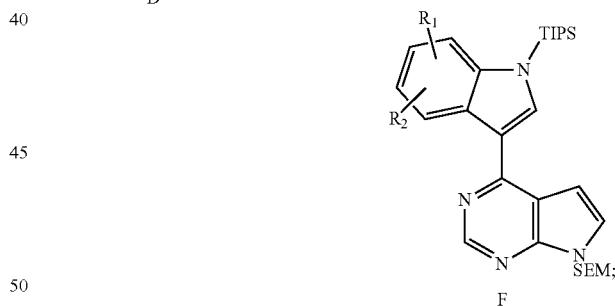

(5) making compound F react with compound G, and taking 1,8-diazabicyclo[5.4.0]undec-7-ene (DBU) as catalyst to form compound H;

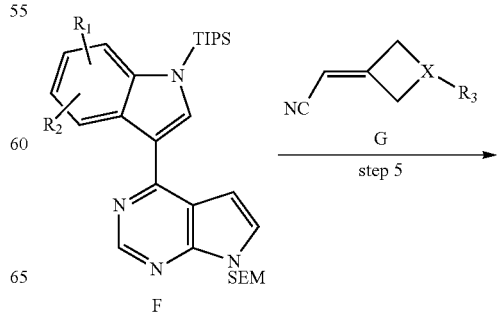

-continued

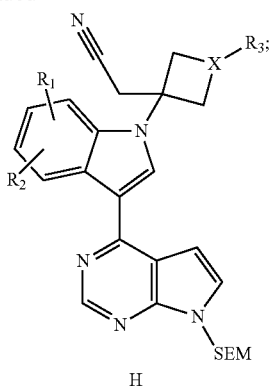

(6) removing protecting group 2-(trimethylsilyl)ethoxymethyl from compound H in presence of strong acid or strong alkaline to obtain the compound of chemical formula I.

3. The compound according to claim 1, which is a pharmaceutically acceptable salt of the compound of chemical formula I.

4. The compound according to claim 1, which is an optical isomer of the compound of chemical formula I.

5. The compound according to claim 3, which is a pharmaceutically acceptable acid addition salt of the compound of formula I.

6. A method of inhibiting JAK-STAT, comprising a step of administering a compound of claim 1 to a human subject suffering from a disease related to JAK-activated kinase.

7. The method according to claim 6, wherein the disease related to JAK-activated kinase is rheumatoid arthritis.

* * * * *